United States Patent [19]
Hirschmann et al.

[11] Patent Number: 5,489,692
[45] Date of Patent: Feb. 6, 1996

[54] PYRROLINONE-BASED COMPOUNDS

[75] Inventors: Ralph Hirschmann, Blue Bell; Amos B. Smith, III, Merion; Paul Sprengeler, Philadelphia, all of Pa.; Ryan C. Holcomb, Glen Rock, N.J.; Terence Keenan, Cambridge; John L. Wood, Quincy, both of Mass.; Mark Guzman, Philadelphia, Pa.

[73] Assignee: The Trustees of the University of Pennsylvania, Philadelphia, Pa.

[21] Appl. No.: 18,696

[22] Filed: Feb. 17, 1993

[51] Int. Cl.$^6$ ............... C07D 207/00; C07D 413/00
[52] U.S. Cl. ................................. 548/519; 544/141
[58] Field of Search .................... 548/519; 544/141

[56] References Cited

U.S. PATENT DOCUMENTS

| | | | |
|---|---|---|---|
| 4,885,292 | 12/1989 | Ryono et al. | 514/211 |
| 5,075,302 | 12/1991 | Neustadt et al. | 514/211 |

OTHER PUBLICATIONS

Smith, III Amos B III JACS 1992, 114 10672–10674.
Karady et al., Enantioretentive Alkylation of Acyclic Amino Acids, Tetrahedron Letters, vol. 25, No. 39, pp. 4337–4340 (1984).
Seebach et al., N,O–Acetals from Pivalaladehyde and Amino Acids for the a–Alkylation with Self Reproduction of the Center of Chirality. Enolates of 3–Benzoyl–2(tertbutyl)–1,3–oxazolidin–5–ones, Helvetica Chimica Acts, vol. 68, pp. 1243–1250 (1985).
Corey et al., Cleavage of Allyloxycarbonyl Protecting Group from Oxygen and Nitrogen under Mild Conditions by Nickel Carbonyl, J. Org. Chem., vol. 38, No. 18, pp. 3223–3224 (1973).
Wlodawer et al., Science, vol. 245, p. 616 (1989).
Renaud et al., J. Biol. Chem., vol. 258, p. 8312 (1983).
Veber et al., J. Org. Chem., vol. 42, p. 3286 (1977).
Atherton et al., J. Org. Chem., vol. 42, p. 3286 (1977).
Kunz et al., "The Allyloxycarbonyl (Aloe) Moiety–Conversion of an Unsuitable into a Valuable Amino Protecting Group for Peptide Synthesis", *Angew. Chem. Int. Ed. Engl.* 23: 436–437 (1984).
Bolis, G. et al., "Renin Inhibitors. Dipeptide analogues of angiotensinogen incorporating transition–state, nonpeptide replacements at the scissile bond" J. Med. Chem. 30: 1729–1737 (1987).
Haber, E. et al., "Renin Inhibitors. A Search for Principles of Design" J. of Cardiovascular Pharm. 10: S54–S58 (1987).
Greene et al., Protective Groups in Organic Synthesis, 2d Ed., John Wiley & Sons, New York (1991).
Gross et al., The Peptide, vol. 9, pp. 1–38, Academic Press, New York, N.Y. (1983).
Iizuka et al., J. Med Chem., vol. 31, p. 701 (1988).
Luly et al., J. Med. Chem. vol. 31, p. 2264 (1988).
Magrath et al., J. Med. Chem., vol. 35, p. 4279 (1992).
Kunz et al., Angew. Chem. Int. Ed. Engl., vol. 7. p. 7 (1968).

*Primary Examiner*—Paul J. Killos
*Attorney, Agent, or Firm*—Woodcock Washburn Kurtz MacKiewicz & Norris

[57] ABSTRACT

Novel pyrrolinone-based compounds mimic or inhibit the biological and/or chemical activity of peptides, including peptide β-strand conformations. Certain compounds contain functionalized pyrrolinone units in place of one or more amino acids of a target peptide.

13 Claims, 3 Drawing Sheets

PYRROLINONE-BASED COMPOUNDS

GOVERNMENT SUPPORT

Certain of the inventors have been supported by National Institutes of Health Grant GM-41821.

FIELD OF THE INVENTION

This invention relates to monomeric and polymeric pyrrolinone-based compounds, to the use of pyrrolinone-based compounds in place of amino acids in naturally-occurring or synthetic peptides, and to methods for preparing such compounds.

BACKGROUND OF THE INVENTION

Peptides are implicated in a wide variety of biochemical processes in humans and other mammals. The design of peptide mimics which are resistant to degradation by proteolytic enzymes has become of increasing interest to peptide chemists. A primary goal has been to reduce the susceptibility of mimics to cleavage and inactivation by peptidases while maintaining certain desired biological, chemical, and/or physical properties of a targeted peptide. As a result, the design and synthesis of non-peptidal peptidomimetics has emerged as an enterprise spanning organic, bioorganic, and medicinal chemistry. Frequently, the design and/or synthetic considerations which attend development of peptide mimics are not easily resolved. For example, there is mounting evidence that hydrogen bonding involving the amide backbones of peptide hormones and their receptors is not required for receptor binding or activation, but that hydrogen bonding involving the amide backbone plays a critical role in the binding of peptidal inhibitors to proteolytic enzymes. Because non-peptidal enzyme inhibitors must mimic both the β-strand conformations and, at least in part, the hydrogen bonding capabilities of their peptide counterparts, the design of such inhibitors is considerably more difficult than the design of non-peptidal hormone-receptor ligands.

There remains a need in the art for metabolically stable chemical compounds which effectively mimic the biological, chemical, and/or physical properties of naturally-occurring or synthetic peptides, particularly those having β-strand conformations.

OBJECTS OF THE INVENTION

It is one object of the present invention to provide compounds that mimic or inhibit the biological and/or chemical activity of peptides.

It is another object to provide compounds that are chemically more stable than peptides, particularly under conditions such as found in the human body.

It is yet another object to provide compounds that can assume the conformation of a β-pleated peptide strand.

It is a further object to provide compounds that function as enzyme inhibitors.

It is yet another object to provide simple yet efficient methods for synthesizing such compounds.

SUMMARY OF THE INVENTION

These and other objects are accomplished by the present invention, which provides pyrrolinone-based compounds that mimic or inhibit the biological and/or chemical activity of a target peptide. In a general sense, the compounds of the invention differ from the target peptide in that they contain functionalized pyrrolinone units in place of one or more peptide amino acids. The compounds can be used to modulate the chemical and/or biological activity of enzymes or other peptides. Indeed, compounds containing covalently bound sequences of pyrrolinone units have been found to mimic the β-strand conformations of a number of naturally occurring peptidal inhibitors of proteolytic enzymes.

In certain embodiments, the pyrrolinone-based compounds of the invention include one or more pyrrolinone units having structures (1) and/or (2):

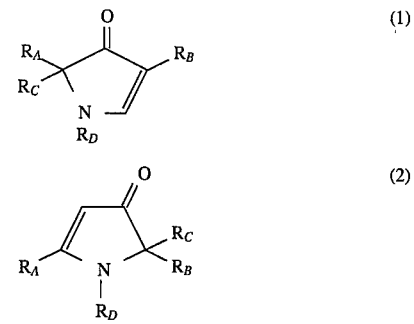

where:

$R_A$ is a C-terminal amino acid, a C-terminal peptide, or a further pyrrolinone unit;

$R_B$ is a N-terminal amino acid, a N-terminal peptide, or a further pyrrolinone unit;

$R_C$ is a naturally-occurring amino acid side chain; and $R_D$ is H, an amine protecting group, or alkyl having 1 to about 7 carbon atoms.

Certain compounds of the invention have structure (3):

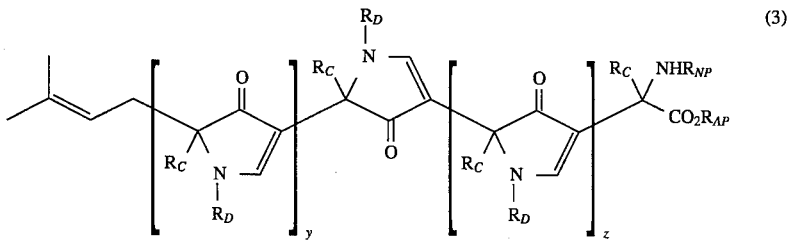

wherein:

each $R_C$ is, independently, an amino acid side chain;

each $R_D$ is, independently, H, an amine protecting group, or alkyl having 1 to about 7 carbon atoms;

$R_{NP}$ is H or an amine protecting group;

$R_{AP}$ is H or a carboxyl protecting group; and y and z are, independently, 0–200.

The compounds of the invention preferably are prepared by a two-step synthesis of 3,5,5-trisubstituted pyrrolin-4-ones that involves intramolecular cyclization of metalated imino esters. The imino esters derive from α-disubstituted amino esters, which preferably are produced by enantioretentive alkylation of oxazolidinones. In certain embodiments, pyrrolin-4-ones having structure (3) are prepared by cyclizing a first synthon having structure (4) and a second synthon having structure (5).

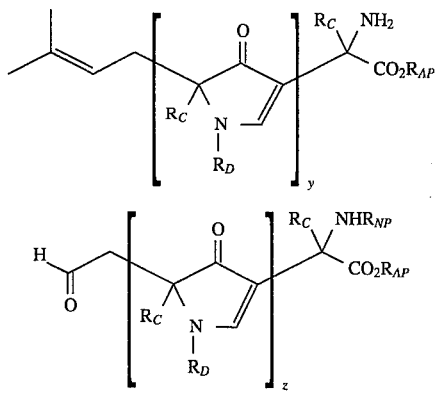

The compounds of the invention are believed to possess beneficial properties such as increased half-life, lack of immunogenicity, and the ability to cross the blood-brain barrier. They are believed to be useful for the development of pharmaceutical, therapeutic, and diagnostic techniques. Accordingly, the invention provides methods for producing a prophylactic or therapeutic response in a mammal by administering to the mammal a pharmaceutically effective amount of one or more compounds of the invention. In accordance with preferred embodiments, the present invention provides methods for producing such responses by administering an effective amount of a compound of the invention, thereby modulating the activity of a mammalian enzyme.

BRIEF DESCRIPTION OF THE FIGURES

The numerous objects and advantages of the present invention can be better understood by those skilled in the art by reference to the accompanying figures, in which.

DETAILED DESCRIPTION OF THE INVENTION

Figure 1:
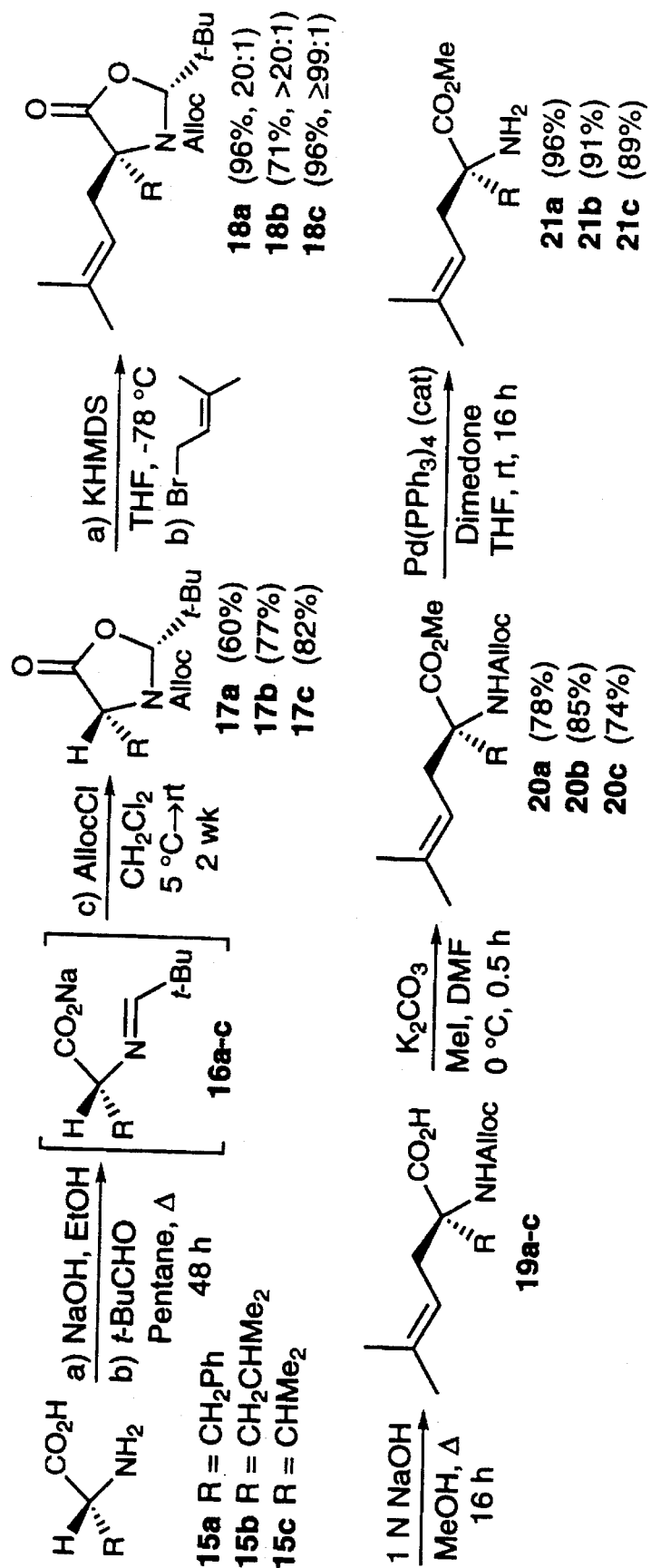
FIG. 1 shows a representative synthesis of acyclic olefinic synthons according to the invention.

It has been found in accordance with the present invention that a new class of compounds containing linked sequences of pyrrolinone units (e.g., structure 6) can adopt backbone conformations that mimic a peptide β-strand, and that peptidal side chains appended to the 5-positions of such units assume desired perpendicular orientations.

By way of example, it is known that structure (7), the crystalline methyl ester of an equine angiotensin fragment, exists as a parallel β-pleated sheet. Comparison of structures (6) and (7) reveals that the disposition of vinylogous amide carbonyls in structure (6) closely correspond with the orientation of the peptide carbonyls in structure (7), maintaining the hydrogen-bond-acceptor capabilities of the native β-strand. The pyrrolinone N—H groups, though vinylogously displaced from the backbone, are comparable to amide nitrogens in basicity and are believed to stabilize the requisite β-strand and β-pleated-sheet conformations through intramolecular and intermolecular hydrogen bonding.

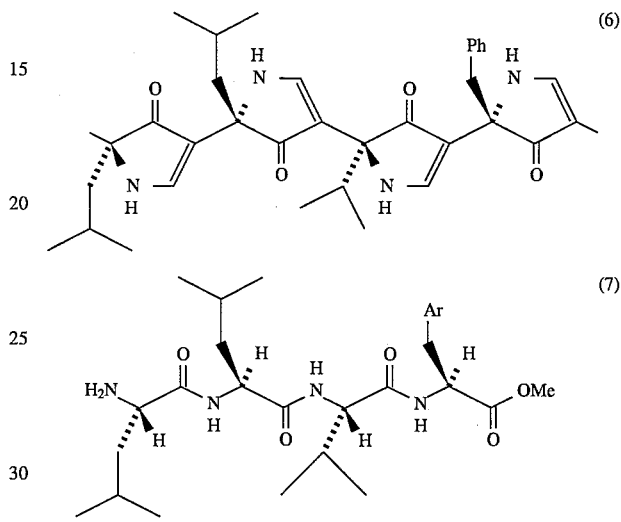

Certain pyrrolinone-based compounds of the invention include one or more pyrrolinone units having structure (1) and/or (2):

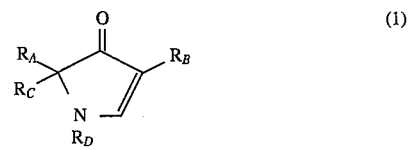

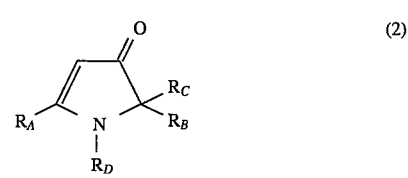

where:

$R_A$ is a C-terminal amino acid, a C-terminal peptide, or a further pyrrolinone unit;

$R_B$ is a N-terminal amino acid, a N-terminal peptide, or a further pyrrolinone unit;

$R_C$ is an amino acid side chain; and $R_D$ is H, an amine protecting group, or alkyl having to about 7 carbon atoms.

In preferred embodiments, compounds of the invention include pyrrolinone-based structures (8a) and (8b):

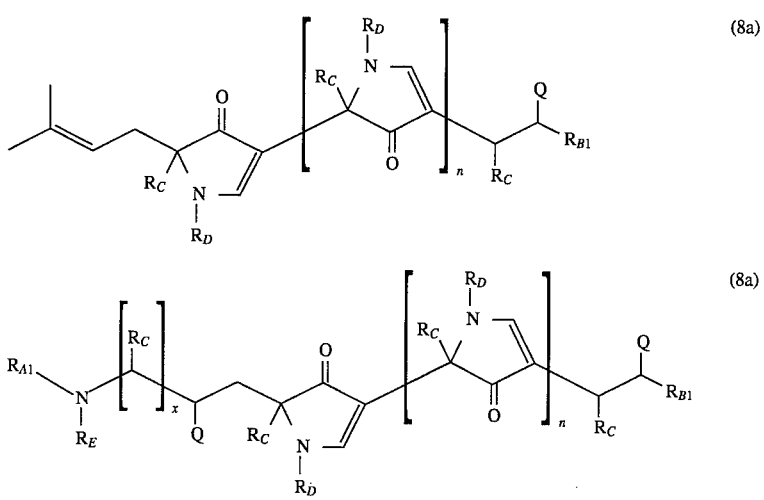

(8a)

(8a)

where:

$R_{A1}$ is H, a C-terminal amino acid, a C-terminal peptide, an amine protecting group, an amide protecting group, a group that improves the pharmacokinetic properties of the compound, or a group that improves the pharmacodynamic properties of the compound;

$R_{B1}$ is $OR_D$, $NR_DR_D$, a N-terminal amino acid, a N-terminal peptide, a carboxyl protecting group, a group that improves the pharmacokinetic properties of the compound, or a group that improves the pharmacodynamic properties of the compound;

each $R_C$ is, independently, an amino acid side chain;

$R_D$ is H, an amine protecting group, or alkyl having 1 to about 7 carbon atoms;

$R_E$ is H or an amine protecting group, or $R_{A1}$ and $R_E$, together are a group that improves the pharmacokinetic properties of the compound or a group that improves the pharmacodynamic properties of the compound;

each Q is, independently, OH or =O;

x is 0 or 1; and n is 0–200.

Representative compounds of the invention have structures (9)–(12). Structure (9a) at 3.5 μM has been found to act as an effective HIV1 inhibitor; structure (11) is expected to find similar use. (see, e.g., Wlodawer, et al., *Science* 1989, 245, 616.). Structure (10a) at 700 nM has been found to act as an effective renin inhibitor. Structure (12) is believed to be an effective serine protease inhibitor (see, e.g., Renaud, et al., *J. Biol. Chem.* 1983, 258, 8312.).

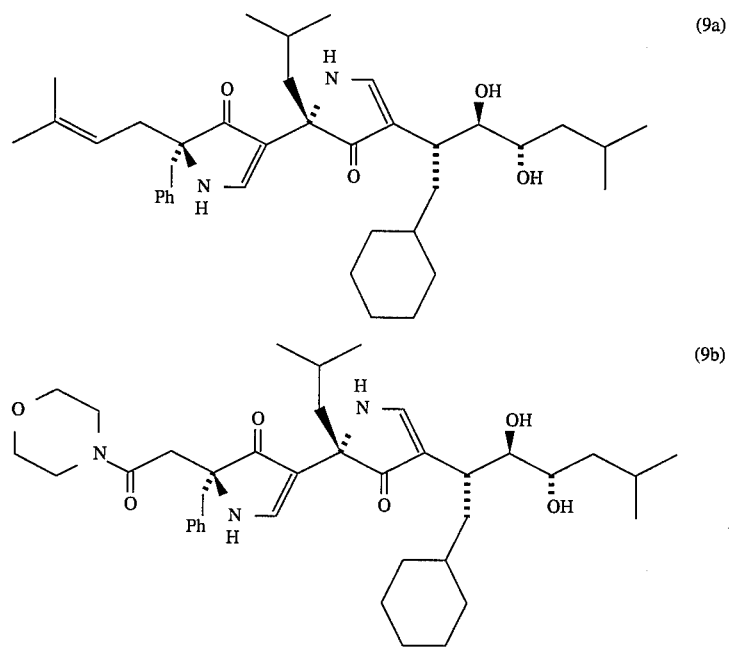

(10a)
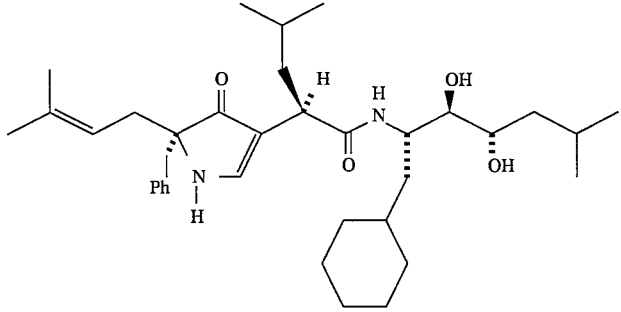

(10b)
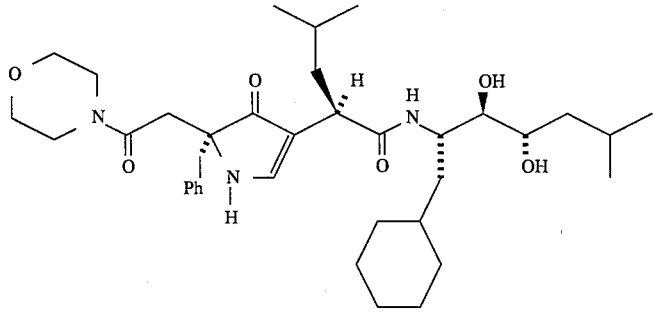

(11)
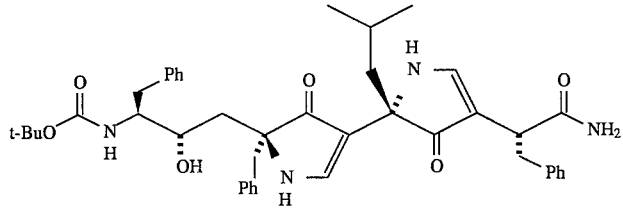

(12)
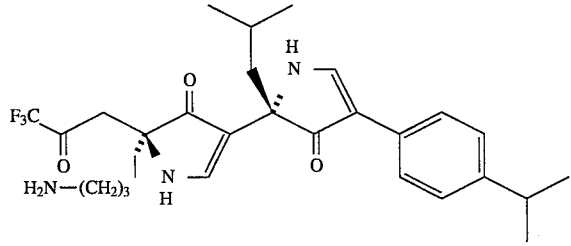

The term amino acid as used herein is intended to include all naturally-occurring and synthetic amino acids known in the art. As will be recognized, amino acids have both C-terminal and N-terminal ends, either of which can be covalently bound to the compounds of the invention. In general, amino acids have structure $H_2N\text{—}CH(R_C)\text{—}C(O)OH$ where $R_C$ is the amino acid side chain. Representative, naturally-occurring side chains are shown in Table 1.

| TABLE 1 | |
|---|---|
| $CH_3-$ | $CH_3-CH_2-S-CH_2-CH_2-$ |
| $HO-CH_2-$ | $HO-CH_2-CH_2-$ |
| $C_6H_5-CH_2-$ | $CH_3-CH_2-(OH)-$ |
| $HO-C_6H_5-CH_2-$ | $HO_2C-CH_2-NH_2C(O)-CH_2-$ |
| 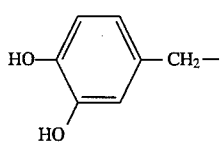 | 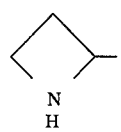 |

TABLE 1-continued

| | |
|---|---|
| 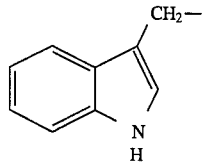 | $HCO_2-CH_2-CH_2-$<br>$NH_2C(O)-CH_2-CH_2-$<br>$(CH_3)_2-CH-$<br>$(CH_3)_2-CH-CH_2-$<br>$CH_3-CH_2-CH_2-$ |
| 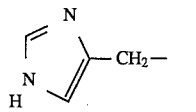 | $H_2N-CH_2-CH_2-CH_2-$<br>$H_2N-C(NH)-NH-CH_2-CH_2-CH_2-$<br>$H_2N-C(O)-NH-CH_2-CH_2-CH_2-$<br>$CH_3-CH_2-CH(CH_3-)-$ |
| $HS-CH_2-$<br>$HO_2C-CH(NH_2)-CH_2-S-S-CH_2-$<br>$CH_3-CH_2-$<br>$CH_3-S-CH_2-CH_2-$ | $CH_3-CH_2-CH_2-CH_2-$<br>$H_2N-CH_2-CH_2-CH_2-CH_2-$ |

Preferred side chains include $C_6H_5$—$CH_2$—, $(CH_3)_2$—CH—, and $(CH_3)_2$—CH—$CH_2$—. Peptides according to the invention are linear, branched, or cyclic chemical structures containing at least 2 covalently bound amino acids. Like individual amino acids, peptides can be incorporated into the compounds of the invention through C-terminal or N-terminal positions.

Alkyl groups according to the invention include but are not limited to straight chain, branched chain, and cyclic hydrocarbons such as methyl, ethyl, propyl, pentyl, isopropyl, 2-butyl, isobutyl, 2-methylbutyl, and isopentyl moieties having 1 to about 12 carbon atoms, preferably 1 to about 7 carbon atoms.

Protecting groups are known per se as chemical functional groups that can be selectively appended to and removed from functionality, such as amine groups, present in a chemical compound to render such functionality inert to chemical reaction conditions to which the compound is exposed. See, e.g., Greene and Wuts, Protective Groups in Organic Synthesis, 2d edition, John Wiley & Sons, New York, 1991. Numerous amine protecting groups are known in the art, including the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschmann, et al., J. Org. Chem. 1977, 42, 3286 and Atherton, et al., The Peptides, Gross and Meienhofer, Eds, Academic Press; New York, 1983; Vol. 9 pp. 1–38). For example, it is known that the Boc group can protect an amine group from base and from reducing conditions but that it can be removed with acid. Carboxyl protecting groups also are known, including lower (i.e., $C_1$–$C_7$) alkyl esters and benzyl esters. Preferred carboxyl protecting groups are stable to acid but can be removed with base.

Groups that improve pharmacokinetic properties are chemical functional groups that improve uptake, enhance resistance to degradation, and/or strengthen enzyme or receptor binding. Groups that enhance pharmacokinetic properties are chemical functional groups that improve uptake, distribution, metabolism or excretion. Indeed, many groups for improving pharmacokinetic and/or pharmacodynamic properties of peptides are known to those skilled in the art. For example, the terminal morpholino and NH—CH($CH_2$-$C_6H_{11}$)—CH(OH)—CH (OH)—$CH_2$—CH($CH_3$)$_2$ groups of structure (10b) have been s et al. J. Med. Chem. 1988, 31, 701, and Luly, et al., J. Med. Chem 1988, 31, 2264, respectively, to improve the binding affinity of renin-inhibiting peptides. Also, Magrath and Abeles, J. Med. Chem. 1992, 35, 4279, disclose use of trifluoromethyl and diazomethyl groups at the C-terminal ($R_{B1}$) position to enhance selectivity for serine and cysteine proteases, respectively.

It will be recognized that the number and structural arrangement of pyrrolinone units in the compounds of the invention can be highly variable. For example, useful mimics for a naturally-occurring tetrapeptide (7) are believed to include poly-pyrrolinone (6) as well as mono-pyrrolinone (13).

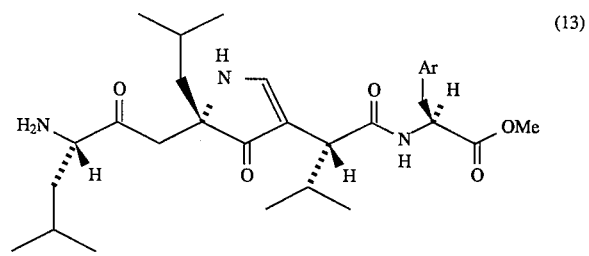

(13)

It is believed that compounds containing a series of at least about 3 covalently bound pyrrolinone units (e.g., n=3) best mimic the β-conformation of a peptide strand, although 2 units are sufficient. However, structure generally is dictated by functional concerns or, more frequently, a balancing of competing functional concerns. Thus, in a hypothetical system in which structures (6) and (13) exhibit comparable binding affinity for a given enzyme but structure (6) exhibits markedly greater stability, structure (6) typically will be preferred. In addition, it will be recognized that 3,5,5-trisubstituted pyrrolin-4-one units (e.g., structure (1)) and 3,3,5-trisubstituted pyrrolin-4-one units (e.g., structure (2)) can be used interchangeably.

In certain embodiments, the compounds of the invention are prepared by a two-step synthesis of scalemic 3,5,5-trisubstituted pyrrolin-4-ones that employs intramolecular cyclization of metalated imino esters. The imino esters, in turn, derive from α-disubstituted amino esters, the latter being readily available via enantioretentive alkylation of oxazolidinones. As shown in FIG. 1, construction of the α-alkylated amino esters begins with formation of the pivaldehyde imines of D-phenylalanine (15a), D-leucine (15b), and D-valine (15c) via the Seebach protocol (see, e.g., Seebach, et al., Helv. Chim. Acta 1985, 68, 1243). Treatment of the imines (16c) with allyl chloroformate generally in accordance with Corey, et al., J. Org. Chem. 1973, 38, 3223, induced cyclization to furnish cis-oxazolidinones (17a–c). Interestingly, exposure to Boc anhydride did not produce the corresponding oxazolidinone. Enantioretentive alkylation as described by Seebach (i.e., KHMDS, prenyl bromide, THF, −78° C.) afforded oxazolidinones (18a–c) with greater than 95% diastereoselectivity. Hydrolysis to Alloc-protected amino acids (19a–c) then was achieved generally according to Karady, et al., *Tetrahedron Lett.* 1984, 25, 4337 (1N NaOH, MeOH, reflux, 16 h), and the resultant acids were immediately methylated [$K_2CO_3$ (2.5 equiv), MeI (2 equiv), DMF, 0.5 h] to furnish esters (20a–c). The Alloc protecting groups could be removed in the presence of the prenyl group with catalytic $Pd(PPh_3)_4$ and dimedone (5 equiv; see, e.g., Kunz, et al., *Angew. Chem. Int. Ed. Engl.* 1968, 7, 7), providing the desired α-alkyl amino esters (21a–c) after Kugelrohr distillation. This sequence is both efficient (42–52% yields for the 6-step sequence) and amenable to large-scale production (ca. 100 g).

Figure 2:
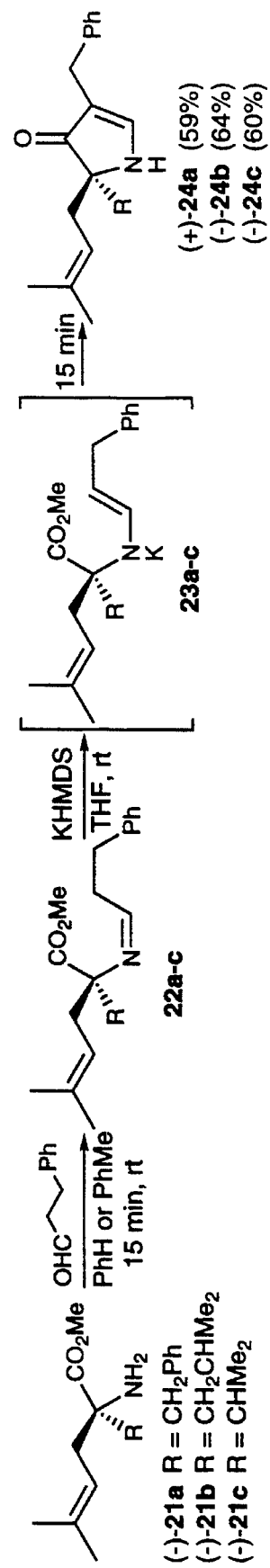
FIG. 2 shows a cyclization procedure according to the invention.

As shown in FIG. 2, amino ester (21a) was condensed with hydrocinnamaldehyde (1.1 equiv) by in vacuo concentration of a benzene or toluene solution of the compounds at ambient temperature; $^1H$ NMR analysis verified the formation of imine (22a). Metalation with KHMDS (THF, room temperature) then furnished metallo imine (23a). Upon stirring at room temperature for 15 min, TLC analysis (20% EtOAc/hexanes) revealed the formation of the desired pyrrolinone (24a), isolable in 59% yield overall from (21a). Similar treatment of the imines derived from amines (21b) and (21c) led to heterocycles (24b) and (24c). The use of lithium diisopropylamide (LDA) for metalation afforded lower yields of the pyrrolinones.

Figure 3:
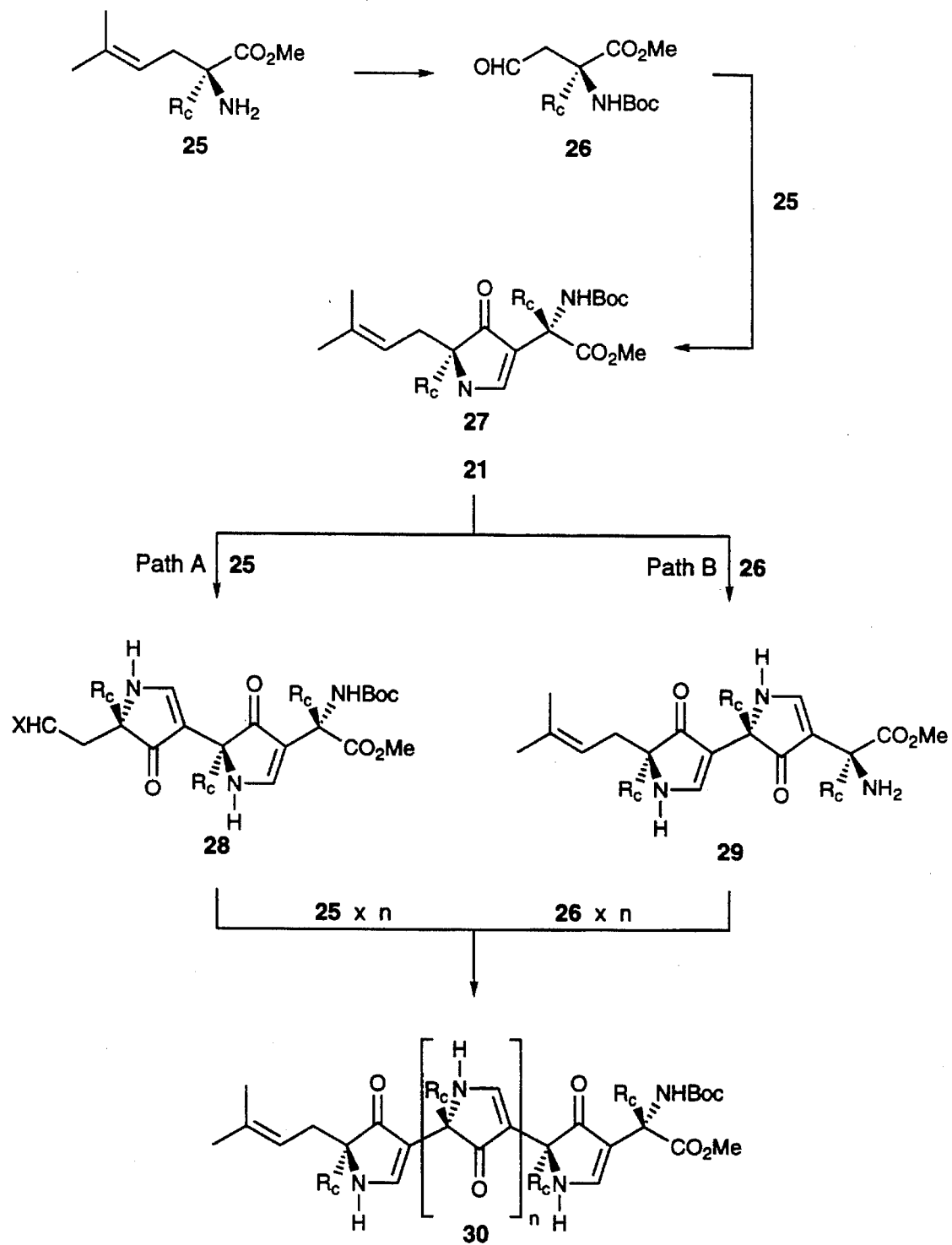
FIG. 3 shows representative syntheses of compounds of the invention via N-terminal and C-terminal cyclizations.

Extension of this procedure to the iterative formation of linked pyrrolinones, as in FIG. 3, can furnish, for example, structure (30) by either "N-terminal" or "C-terminal" elaboration. As will be recognized, N-terminal elaboration is exemplified by Path A, wherein X=$O_2$Me (28a) or X=O (28b), and C-terminal elaboration is exemplified by Path B.

The pyrrolinone-based compounds of the invention contain amino groups and, therefore, are capable of forming salts with various inorganic and organic acids. Such salts are also within the scope of this invention. Representative salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

The present invention also provides prophylactic, diagnostic, and therapeutic compositions comprising one or more pyrrolinone-based compounds. By administering an effective amount of such compositions, for example, prophylactic or therapeutic responses can be produced in a human or some other type mammal. It will be appreciated that the production of prophylactic or therapeutic responses includes the initiation or enhancement of desirable responses, as well as the cessation or suppression of undesirable responses.

Compositions for use in the methods of this invention can be in the form of a solid, semisolid or liquid form and can include one or more of pyrrolinone-based compounds as an active ingredient in admixture with an organic or inorganic carrier or excipient suitable for external, enteral or parenteral applications. The active ingredient can be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes maybe used. The active ingredient is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of pyrrolinone-based compounds in either sesame or peanut oil or in aqueous propylene glycol can be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is possible to administer the compounds of the present invention topically when treating inflammatory conditions of the skin and this may preferably be done by way of creams, jellies, gels, pastes, ointments and the like, in accordance with standard pharmaceutical practice.

The amount of active ingredient that may be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day.

Additional objects, advantages, and novel features of this invention will become apparent to those skilled in the art upon examination of the following examples thereof, which are not intended to be limiting.

EXAMPLE 1

Preparation of Oxazolidinones

A. Oxazolidinone Derived from D-Leucine, Structure (17b)

A solution of 7.62 g (191 mmol) of NaOH in 50 mL of $H_2O$ was added to a solution of 25.0 g (191 mmol) of D-leucine in 400 mL of 95% ethanol. The solution was heated gently to ensure dissolution and then concentrated under reduced pressure until precipitation began. The resulting slurry was diluted with 500 mL of pentane followed by addition of 31.1 mL (286 mmol) of pivaldehyde. The flask was then fitted with a Dean-Stark trap and a condenser and the mixture was heated at reflux until water ceased to be collected (about 48 h). The mixture was then allowed to cool and concentrated under reduced pressure to afford a white powder. Toluene was added and removed under reduced pressure to complete the drying process and the solid was stored under vacuum overnight.

The dried salt was treated with 400 mL of $CH_2Cl_2$ and the mixture was cooled to 0° C. Allyloxychloroformate (30.3 mL, 286 mmol) was then added and the slurry stirred at 5° C. for fourteen days followed by an additional two days at room temperature. The mixture was diluted with 100 mL of ethyl acetate (EtOAc) and 100 mL of saturated $NaHCO_3$ solution then 50 mg of dimethylaminopyridine (DMAP) was added to catalyze the hydrolysis of excess allyloxychloroformate. The mixture was stirred for three hours, the layers separated, and the organic layer washed with 150 mL of a 10% aqueous $NaHSO_4$ solution and saturated aqueous $NaHCO_3$ solution (2×150 mL). The organic layer was dried over anhydrous $MgSO_4$ then concentrated under reduced pressure to afford 49.0 g of a yellow oil. The oil was dissolved in hexanes and cooled in a dry ice bath to provide 23.49 g of a white crystalline powder. The mother liquour was concentrated and subjected to flash chromatography (silica, 10% EtOAc/hexanes) to afford an additional 4.47 g of the solid oxazolidinone providing a total yield of 32.36 g (60% yield) of pure oxazolidinone as a single diastereomer: m.p. 37°–39° C.; $[\alpha]_D^{20}$–43.9° (c. 3.05, $CHCl_3$); $^1H$ NMR (500 MHZ, $CDCl_3$) d 5.97–5.89 (m, 1 H), 5.55 (s, 1 H), 5.35 (dd, J=17.2 and 1.3 Hz, 1 H), 5.28 (dd, J=10.4 and 0.6 Hz, 1 H), 4.65 (d, J=6.0 Hz, 2 H), 4.35 (dd, J=7.4 and 6.6 Hz, 1 H), 2.07–2.03 (m, 1 H), 1.84–1.78 (m, 1 H), 1.70–1.65 (m, H), 1.01 (d, J=1.9 Hz, 3 H), 0.99 (d, J=1.9 Hz, 3 H), 0.99 (s, 9 H); $^{13}C$ NMR (125 MHz, $CDCl_3$) d 172.95, 155.87, 131.72, 119.16, 96.23, 67.08, 55.49, 42.43, 36.88, 25.01, 24.93 (3C), 22.73, 22.04; IR ($CHCl_3$) 3000, 2880, 1800, 1720, 1655, 1470 cm$^{-1}$; high resolution mass spectrum (CI, methane) m/z 284.1839 [(M+H)$^+$; calculated for $C_{15}H_{26}NO_4$: 284.1862]. Analysis calculated for $C_{15}H_{25}NO_4$: C, 63.58; H, 8.89; N, 4.94; found: C, 63.81; H, 8.90;N, 4.83.

B. Oxazolidinone Derived from D-Phenylalanine, Structure (17a)

Following the procedure of Example 1A, 15.3 g (92.6 mmol) of D-phenylalanine, 3.70 g (96.6 mmol) of NaOH, and 15.1 mL (139 mmol) of pivaldehyde afforded the Schiff-Base salt of D-phenylalanine. Oxazolidinone formation was promoted using 14.7 mL (139 mmol) of allyloxychloroformate over a ten day period at 5° C. then two days at room temperature to afford 26.51 g of crude product with high diastereomeric purity. Flash chromatography (silica, 10% EtOAc/hexanes) provided 22.50 g (77% yield) of pure oxazolidinone: $[\alpha]_D^{20}$–1.63° (c 8.77, $CHCl_3$); IR ($CHCl_3$) 1800, 1725, 1480, 1450, 1380 cm$^{-1}$; $^1H$ NMR (500 MHz, $CDCl_3$) d 7.34–7.20 (m, 5 H), 5.80–5.72 (m, 1 H), 5.56 (s, 1 H), 5.28–5.21 (m, 2 H), 4.54 (dd, J=12.9 and 6.1 Hz, 1 H), 4.51 (dd, J=7.4 and 5.9 Hz, 1 H), 4.43 (dd, J= 12.4 and 5.7 Hz, 1 H), 3.25 (dd, J=13.9 and 7.4 Hz, 1 H), 3.13 (dd, J=13.9 and 5.9 Hz, 1 H), 1.02 (s, 9 H); $^{13}C$ NMR (125 MHz, $CDCl_3$) d 171.87, 155.69, 136.84, 131.64, 129.49 (2C), 128.44 (2C), 126.94, 119.04, 96.24, 67.05, 58.91, 39.21, 37.03, 24.92 (3C); high resolution mass spectrum (CI, $NH_3$) m/z 335.1970 [(M+$NH_4$)$^+$; calculated for $C_{18}H_{27}N_2O_4$: 335.1970]. Analysis calculated for $C_{18}H_{23}NO_4$: C, 68.12; H, 7.30;N, 4.41; found: C, 68.23; H, 7.44;N, 4.60.

C. Oxazolidinone Derived from D-Valine, Structure (17c)

Following the procedure of Example 1A, 25.0 g (213 mmol) of D-valine, 8.54 g (213.4 mmol) of NaOH, and 34.8 mL (320 mmol) of pivaldehyde provided the Schiff-Base salt of D-valine. Oxazolidinone formation was promoted using 34.0 mL (320 mmol) of allyloxychloroformate over a fourteen day period at 5° C. then overnight at room temperature to afford the crude product with high diastereoselectivity. Flash chromatography (silica, 10% EtOAc/hexanes) afforded 47.38 g (82% yield) of pure oxazolidinone: $[\alpha]_D^{20}$–14.42° (c 12.78, $CHCl_3$); IR ($CHCl_3$) 1785, 1710, 1465 cm$^{-1}$; $^1H$ NMR (500 MHz, $CDCl_3$) d 5.97–5.89 (m, 1 H), 5.56 (s, 1 H), 5.35 (ddd, J=17.2, 2.8, and 1.40 Hz, 1 H), 5.29 (ddd, J=11.6, 2.4, and 1.2 Hz, 1 H), 4.65 (dt, J=5.9 and 1.3 Hz, 2 H), 3.98 (d, J=10.9 Hz, 1 H), 2.05–1.98 (m, 1 H), 1.27 (d, J=6.4 Hz, 3 H), 1.09 (d, J=6.9 Hz, 3 H), 1.00 (s, 9 H); $^{13}C$ NMR (125 MHz, $CDCl_3$) d 172.17, 156.50, 131.70, 119.01, 96.21, 67.18, 61.94, 36.59, 31.94, 24.95 (3C), 19.80, 19.52; high resolution mass spectrum (CI, $NH_3$) m/z 270.1683 [(M+H)$^+$ calculated for $C_{14}H_{24}NO_4$: 270.1705]. Analysis calculated for $C_{14}H_{23}NO_4$: C, 62.43; H, 8.61;N, 5.20; found: C, 62.70; H, 8.57;N, 4.83.

EXAMPLE 2

Alkylation of Oxazolidinones

A. Alkylation of Oxazolidinone Derived from D-Leucine

A solution of 11.5 g (40.6 mmol) oxazolidinone derived from D-leucine in 150 mL of tetrahydrofuran (THF) was cooled in a dry ice/ether bath to −78° C. To this solution was added 97.4 mL (48.7 mmol) of a 0.5M potassium 1,1,1,3,3,3-hexamethyldisilazine (KHMDS) solution in toluene via a dropping funnel at a rate so as to maintain an internal temperature no higher than −70° C. The resulting yellow solution was stirred at −78° C. for 15 min after which time 12.1 mL (81.2 mmol) of 1-bromo-3-methyl-2-butene was added dropwise, again maintaining a temperature no higher than −70° C. The solution was stirred for 30 min at −78° C. then quenched with 300 mL of a 10% aqueous $NaHSO_4$ solution. The mixture was extracted with EtOAc (2×100 mL) and the organic phases washed with 10% aqueous $NaHSO_4$ solution (2×200 mL), saturated aqueous $NaHCO_3$ solution (1×200 mL), and 200 mL of a saturated aqueous NaCl solution. Drying over anhydrous $MgSO_4$ followed by concentration under reduced pressure afforded 15.93 g crude product which was purified by flash chromatography (silica, 10% EtOAc/hexanes) to provide 13.8 g (96% yield) of pure alkylation product, structure (18b): $[\alpha]_D^{20}$+25.6° (c 6.13, CHCl$_3$); IR (CHCl$_3$) 1790, 1720, 1450, 1390, 1190 cm$^{-1}$; $^1$H NMR (500 MHz, CDCl$_3$) d 5.96–5.90 (m, 1 H), 5.43 (s, 1 H), 5.36 (dd, J=17.1 and 0.7 Hz, 1 H), 5.28 (dd, J=10.4 and 0.8 Hz, 1 H), 4.82 (t, J=6.9 Hz, 1 H), 4.68 (dd, J=12.9 and 5.6 Hz, 1 H), 4.51 (dd, J=12.8 and 5.7 Hz, 1 H), 3.1 (br s, 1 H), 2.47 (dd, J=14.0 and 5.5 Hz, 1 H), 2.1 (br s, 1 H), 1.96 (dd, J=14.5 and 5.7 Hz, 1 H), 1.90 (dd, J=14.6 and 5.2 Hz, 1 H), 1.68 (s, 3 H), 1.58 (s, 3 H), 1.06–0.91 (m, 15 H); $^{13}$C NMR (125 MHz, CDCl$_3$) d 174.75, 154.91 (br), 137.86, 131.84, 118.93, 116.03, 95.13, 67.39, 66.49, 46.18, 37.96, 35.50 (br), 26.12, 25.66 (3C), 24.88, 24.63, 23.73, 18.05; high resolution mass spectrum (CI, NH$_3$) m/z 369.2727 [(M+NH$_4$)$^+$; calculated for C$_{20}$H$_{37}$N$_2$O$_4$: 369.2753]. Analysis calculated for C$_{20}$H$_{33}$NO$_4$: C, 68.34; H, 9.46;N, 3.99; found: C, 68.33; H, 9.81;N, 3.75.

B. Alkylation of Oxazolidinone Derived from D-Phenylalanine

Following the procedure of Example 2A, 6.00 g (18.9 mmol) of the oxazolidinone derived from D-phenylalanine, 45.4 mL (22.7 mmol) of a 0.5M KHMDS solution in toluene, and 5.63 g (37.8 mmol) of 1-bromo-3-methyl-2-butene provided 5.19 g (71% yield) of alkylation product, structure (18a), after flash chromatography (silica, 10% EtOAc/hexanes): $[\alpha]_D^{20}$–19.65° (c 13.57, CHCl$_3$); IR (CHCl$_3$) 1795, 1720, 1490, 1450 cm$^{-1}$; $^1$H NMR (500 MHz, CDCl$_3$) d 7.35–7.18 (m, 5 H), 5.98–5.92 (m, 1 H), 5.45–5.25 (m, 3 H), 4.89 (dd, J=8.1 and 7.2 Hz, 1 H), 4.73 (dd, J=12.9 and 5.9 Hz, 1 H), 4.58 (br m, 1 H), 3.38 (br s, 1 H), 3.30 (d, J=13.7 Hz, 1 H), 3.05 (br s, 1 H), 2.48 (br s, 1 H), 1.69 (s, 3 H), 1.58 (s, 3 H), 0.55 (s, 9 H); $^{13}$C NMR (125 MHz, CDCl$_3$) d 173.68, 155.40 (br), 138.24, 135.86, 131.67, 130.99 (2C), 128.24 (2C), 127.10, 119.24, 115.53, 95.18, 69.13, 66.61, 42.07, 37.52, 36.28 (br), 26.08, 24.95 (3C), 17.93; high resolution mass spectrum (CI, NH$_3$) m/z 403.2529 [(M+NH$_4$)$^+$; calculated for C$_{23}$H$_{35}$N$_2$O$_4$: 403.2596]. Analysis calculated for C$_{23}$H$_{31}$NO$_4$: C, 71.66; H, 8.10;N, 3.63; found: C, 71.50; H, 8.39;N, 3.63.

C. Alkylation of the Oxazolidinone Derived from D-Valine

Following the procedure of Example 2A, 6.70 g (24.9 mmol) of the oxazolidinone derived from D-valine, 60.0 mL (29.9 mmol) of a 0.5M KHMDS solution in toluene, and 7.45 g (50.0 mmol) of 1-bromo-3-methyl-2-butene provided 8.08 g (96% yield) of pure alkylation product, structure (18c), after flash chromatography (silica, 10% EtOAc/hexanes): $[\alpha]_D^{20}$+ 16.42° (c 13.18, CHCl$_3$); IR (CHCl$_3$) 1785, 1710, 1450, 1380 cm$^{-1}$; $^1$H NMR (500 MHz, CDCl$_3$) d 5.95–5.87 (m, 1 H), 5.48 (s, 1 H), 5.34 (ddd, J=17.2, 2.8, and 1.4 Hz, 1 H), 5.28 (ddd, J= 10.4, 2.3, and 1.0 Hz, 1 H), 4.75–4.71 (m, 1 H), 4.66 (ddt, J=13.0, 5.9, and 1.2 Hz, 1 H), 4.46 (ddt, J=13.0, 6.0, and 1.2 Hz, 1 H), 3.08 (dd, J=14.4 and 8.0 Hz, 1 H), 2.55 (dd, J=14.7 and 6.1 Hz, 1 H), 2.38–2.32 (m, 1 H), 1.77 (s, 3 H), 1.60 (s, 3 H), 1.17 (d, J=3.3 Hz, 3 H), 1.16 (d, J=3.2 Hz, 3 H), 0.99 (s, 9 H) ; $^{13}$C NMR (125 MHZ, CDCl$_3$) d 174.30, 154.98, 137.69, 131.94, 118.93, 116.27, 95.09, 70.09, 66.58, 37.72, 35.54, 29.98 (br), 26.16, 25.94 (3C), 18.82, 18.52, 18.19; high resolution mass spectrum (CI, methane) m/z 338.2298 [(M+H)$^+$; calculated for C$_{19}$H$_{32}$NO$_4$: 338.2331]. Analysis calculated for C$_{19}$H$_{31}$NO$_4$; C, 67.63; H, 9.26;N, 4.15; found: C, 67.77; H, 9.44;N, 4.15.

EXAMPLE 3

Hydrolysis and Esterification of Oxazolidinones

A. Alloc-Protected Amino Ester Derived from D-Leucine

A solution of 2.00 g (5.69 mmol) of the prenylated oxazolidinone derived from D-leucine in 30 mL of methanol and 30 mL of a 1N aqueous NaOH solution was heated at reflux for 16 h. The solution was then allowed to cool and concentrated under reduced pressure. The residue was acidified with 10% aqueous NaHSO$_4$ and then extracted with EtOAc (3×50 mL). The organic phases were combined and washed with 50 mL of H$_2$O and 50 mL of a saturated aqueous NaCl solution, then dried over anhydrous MgSO$_4$ and concentrated to afford a crude residue.

The crude residue was dissolved in 5.0 mL of DMF and 2.0 g of anhydrous K$_2$CO$_3$ was added. The mixture was then cooled to 0° C. and 0.71 mL (11.4 mmol) iodomethane added slowly. The resulting yellow mixture was stirred at 0° C. for 30 min then at room temperature for 30 min. The reaction was quenched with 10 mL of H$_2$O and extracted with ether (2×50 mL). The organic phases were combined and washed with H$_2$O (4×50 mL), 50 mL of a saturated aqueous NaHCO$_3$ solution, and 50 mL of a saturated aqueous NaCl solution, then dried over anhydrous MgSO$_4$ and concentrated to a thick oil. Flash chromatography (silica, 10% EtOAc/hexanes) provided 1.31 g (78% yield) of ester, structure (20b): $[\alpha]_D^{20}$+41.8° (c 16.1, CHCl$_3$); IR (CHCl$_3$) 3500, 3420, 2900, 1720, 1650, 1500 cm$^{-1}$; $^1$H NMR (500 MHz, CDCl$_3$) d 5.93–5.88 (m, 2H), 5.30 (d, J=17.2 Hz, 1 H), 5.20 (d, J=10.3, 1 H), 4.89 (br t, 1 H), 4.53 (d, J=3.77 Hz, 2 H), 3.73 (s, 3 H), 3.02 (dd, J=14.1 and 7.1 Hz, 1 H), 2.42–2.38 (m, 2 H), 1.71–1.66 (obs m, 1 H), 1.66 (s, 3 H), 1.60–1.56 (obs m, 1 H), 1.58 (s, 3 H), 0.89 (d, J=6.6 Hz, 3 H), 0.78 (d, J=6.6 Hz, 3 H); $^{13}$C NMR (125 MHz, CDCl$_3$) d 174.58, 153.70, 135.44, 132.98, 117.57, 117.15, 64.80, 63.45, 52.24, 43.62, 35.28, 25.82, 24.45, 23.70, 22.35, 17.65; high resolution mass spectrum (CI, methane) m/z 298.2019 [(M+H)$^+$; calculated for C$_{16}$H$_{28}$NO$_4$: 298.2018]. Analysis calculated for C$_{16}$H$_{27}$NO$_4$: C, 64.62; H, 9.15;N, 4.71; found: C, 64.95; H, 9.23;N, 4.64.

B. Alloc Protected Amino Ester Derived from D-Phenylalanine

Following the procedure of Example 3A, 5.00 g (13.0 mmol) of the prenylated oxazolidinone derived from D-phenylalanine followed by 5.0 g of anhydrous K$_2$CO$_3$ and 1.62 mL (26.0 mmol) of iodomethane afforded 3.76 g (85% yield) of ester, structure (20a), after flash chromatography (silica, 10% EtOAc/hexanes): $[\alpha]_D^{20}$–23.6° (c 7.24, CHCl$_3$); IR (CHCl$_3$) 3500, 3460, 2900, 1725, 1650, 1500 cm$^{-1}$; $^1$H NMR (500 MHz, CDCl$_3$) d 7.27–7.20 (m, 5 H), 5.97–5.88 (m, 1 H), 5.59 (s, 1 H), 5.30 (d, J=17.2 Hz, 1 H), 5.21 (d, J=10.5 Hz, 1 H), 4.96 (t, J=7.3, 1 H), 4.61, (dd, J=13.5 and 5.4 Hz, 1 H), 4.54 (dd, J=13.4 and 5.2 Hz, 1 H), 3.72 (s, 3 H), 3.65 (d, J=13.6 Hz, 1 H), 3.20–3.13 (ohs m, 1 H), 3.13 (d, J=13.6 Hz, 1 H), 2.59 (dd, J=14.1 and 7.1 Hz, 1 H), 1.67 (s, 3 H), 1.60 (s, 3 H); $^{13}$C NMR (125 MHz, CDCl$_3$) d 172.93, 154.08, 136.20, 135.71, 132.93, 129.59 (2C), 128.06 (2C), 126.71, 117.46, 117.23, 65.09, 64.87, 52.27, 40.50, 34.39, 25.84, 17.76; high resolution mass spectrum (CI, NH$_3$) m/z 332.1841 [(M+H)$^+$; calculated for C$_{19}$H$_{26}$NO$_4$: 332.1862]. Analysis calculated for C$_{19}$H$_{25}$NO$_4$: C, 68.86; H, 7.60; N, 4.23; found: C, 68.76; H, 7.49; N, 3.92.

C. Alloc Protected Amino Ester Derived from D-Valine

Following the procedure of Example 3A, 30.0 g (111 mmol) of the prenylated oxazolidinone derived from D-valine followed by 30 g of anhydrous $K_2CO_3$ and 31.6 g (222 mmol) of iodomethane afforded 20.0 g (63% yield) of ester, structure (20c), after flash chromatography (silica, 10% EtOAc/hexanes): $[\alpha]_d^{20}$+22.36° (c 18.36, $CHCl_3$); IR ($CHCl_3$) 3460, 2900, 1720, 1650, 1490, 1440 cm$^{-1}$; $^1$H NMR (500 MHz, $CDCl_3$) d 5.94–5.86 (m, 1 H), 5.75 (br s, 1 H), 5.29 (ddd, J=17.3, 3.1, and 1.5 Hz, 1 H), 5.19 (dd, J=10.5 and 1.3 Hz, 1 H), 4.90 (m, J=6.0 Hz, 1 H), 4.56–4.45 (m, 2 H), 3.73 (s, 3 H), 3.12 (dd, J= 13.7 and 6.6 Hz, 1 H), 2.65 (dd, J=14.5 and 7.3 Hz, 1 H), 2.50–2.44 (m, 1 H), 1.65 (s, 3 H), 1.58 (s, 3 H), 0.98 (d, J =6.9 Hz, 3 H), 0.90 (d, J=6.9 Hz, 3 H); $^{13}$C NMR (125 MHz, $CDCl_3$) d 173.01, 153.76, 134.60, 132.86, 118.20, 116.79, 67.03, 64.61, 51.86, 33.44, 30.69, 25.68, 17.57, 17.51, 17.46; high resolution mass spectrum (CI, methane) m/z 284.1877 [(M+H)$^+$; calculated for $C_{15}H_{26}NO_4$: 284.1862]. Analysis calculated for $C_{15}H_{25}NO_4$: C, 63.58; H, 8.89; N, 4.94; found: C, 63.67; H, 9.17; N, 4.83.

EXAMPLE 4

Deprotection of N-Alloc Protected Amino Esters

A. Amino Ester Derived from D-Leucine

A mixture of 3.33 g (11.2 mmol) of the N-Alloc protected amino ester derived from D-Leucine, 7.9 g (56 mmol) of dimedone, 46 mg (0.04 mmol) of $Pd(PPh_3)_4$, and 50 mL of THF was stirred at room temperature for 16 h then diluted with 100 mL of ether and extracted with an aqueous 1N HCl solution (5×75 mL). The aqueous layers were combined, made basic by addition solid $K_2CO_3$, then extracted with EtOAc (3×100 mL). The organic layers were combined and washed with 100 mL of a saturated aqueous $NaHCO_3$ and NaCl solutions, then dried over anhydrous magnesium sulfate and concentrated under reduced pressure to afford a light brown oil. The oil was subjected to Kugelrohr distillation (heat gun, 0.01 mm Hg) to provide 2.30 g (96% yield) of pure amino ester, structure (21c), as a colorless oil: $[\alpha]_D^{20}$+34.4° (C 7.48, $CHCl_3$); IR ($CHCl_3$) 3380, 3220, 2980, 1735, 1605, 1450 cm$^{-1}$; $^1$H NMR (500 MHz, $CDCl_3$) d 5.01–4.98 (m, 1 H), 3.69 (s, 3 H), 2.43 (dd, J=14.0 and 6.6 Hz, 1 H), 2.25 (dd, J=14.0 and 8.7 Hz, 1 H), 1.76–1.71 (m, 2 H), 1.70 (s, 3 H), 1.62 (s, 3 H), 1.61–1.50 (m, 4 H), 0.94 (d, J=6.4 HZ, 3 H), 0.82 (d, J=6.3 Hz, 3 H); $^{13}$C NMR (125 MHZ, $CDCl_3$) d 177.74, 135.60, 117.72, 60.47, 51.30, 48.32, 39.47, 25.59, 24.23, 23.82, 22.19, 17.54; high resolution mass spectrum (CI, methane) m/z 214.1790 [(M+H)$^+$; calculated for $C_{12}H_{24}NO_2$: 214.1807]. Analysis calculated for $C_{12}H_{23}NO_2$: C, 67.57; H, 10.87; N, 6.57; found: C, 67.58; H, 11.00; N, 6.51.

B. Amino Ester Derived from D-Phenylalanine

Following the procedure of Example 4A, 11.9 g (35.9 mmol) of the Alloc protected amino ester derived from D-phenylalanine, 15.1 g (108 mmol) of dimedone, and 750 mg (0.65 mmol) of $Pd(PPh_3)_4$ afforded 8.18 g (91% yield) of the free amino ester, structure (21a), as a crystalline solid after Kugelrohr distillation: mp 44°–45° C., b.p. <150°/0.01 mm Hg; $[\alpha]_D^{20}$-2.58° (c 4.53, $CHCl_3$); IR ($CHCl_3$) 3360, 1735, 1600, 1500, 1445 cm$^{-1}$; $^1$H NMR (500 MHz, $CDCl_3$) d 7.30–7.10 (m, 5 H), 5.07–5.03 (m, 1 H), 3.68 (s, 3 H), 3.18 (d, J=13.1 Hz, 1 H), 2.79 (d, J=13.2 Hz, 1 H), 2.60 (dd, J=14.1 and 6.7 Hz, 1 H), 2.48 (dd, J=14.1 and 8.5 Hz, 1 H), 1.73 (s, 3 H), 1.67 (s, 3 H), 1.53 (br s, 2 H); $^{13}$C NMR (125 MHz, $CDCl_3$) d 176.92, 136.50, 136.37, 129.84 (2C), 128.32 (2C), 126.86, 117.95, 62.57, 51.84, 45.92, 38.73, 26.04, 18.05; high resolution mass spectrum (CI, $NH_3$) m/z 248.1654 [(M+H)$^+$; calculated for $C_{15}H_{22}NO_2$: 248.1650]. Analysis calculated for $C_{15}H_{21}NO_2$: C, 72.84; H, 8.56; N, 5.66; found: C, 72.89; H, 8.70; N, 5.65.

C. Amino Ester Derived from D-Valine

Following the procedure of Example 4A, 20.0 g (70.3 mmol) of the Alloc protected amino ester derived from D-valine, 19.7 g (141 mmol) of dimedone, and 406 mg (0.035 mmol) of $Pd(PPh_3)_4$ afforded 12.0 g (86% yield) of the free amino ester, structure (21c), as a viscous oil after Kugelrohr distillation: $[\alpha]_D^{20}$-10.82° (C 13.22, $CHCl_3$); IR ($CHCl_3$) 3500, 3380, 3300, 1720, 1600 cm$^{-1}$; $^1$H NMR (500 MHz, $CDCl_3$) d 5.00 (m, 1 H), 3.70 (s, 3 H), 2.39 (dd, J=14.1 and 6.7 Hz, 1 H), 2.32 (dd, J=14.1 and 8.4 Hz, 1 H), 2.03 (m, 1 H), 1.70 (s, 3 H), 1.64 (s, 3 H), 1.43 (br s, 1 H), 0.96 (d, J=6.8 Hz, 3 H), 0.84 (d, J=6.9 Hz, 3 H); $^{13}$C NMR (125 MHz, $CDCl_3$) d 177.48, 136.50, 118.48, 64.29, 51.49, 35.98, 35.17, 25.77, 17.68, 17.62, 15.94; high resolution mass spectrum (CI, methane) m/z 200.1658 [(M+H)$^+$; calculated for $C_{11}H_{22}NO_2$: 200.1650]. Analysis calculated for $C^{11}H_{21}NO_2$: C, 66.30; H, 10.62; N, 7.03; found: C, 66.06; H, 10.57; N, 7.00.

EXAMPLE 5

BOC Protection of Amino Esters

A. Boc Protected Amino Ester Derived from D-Leucine

A solution of 1.72 g (8.06 mmol) of the amino ester derived from D-leucine and 2.20 g (10.1-mmol) of di-tert-butyl dicarbonate in 15 mL of THF was heated at reflux for 16 h. The solution was allowed to cool and 15 mL of $H_2O$ and 20 mg of DMAP was added to catalyze the hydrolysis of excess di-tert-butyl dicarbonate. After 30 minutes the mixture was extracted with EtOAc (2×25 mL) and the Organic layers combined and washed with 10% aqueous $NaHSO_4$ (2×25 mL), saturated aqueous $NaHCO_3$ and NaCl solutions (2×25 mL). The organic phase was dried over $MgSO_4$ and concentrated to an oil. Flash chromatography (silica, 10% EtOAC/hexanes) provided 2.37 g of the Boc-protected amino ester derived from D-leucine. (94% yield) of a clear colorless oil: $[\alpha]_D^{20}$+34.6° (c 7.48, $CHCl_3$); IR ($CHCl_3$) 3420, 1720, 1500, 1450 cm$^{-1}$; $^1$H NMR (500 MHz, $CDCl_3$) d 5.61 (br s, 1 H), 4.88 (br s, 1 H), 3.74 (s, 3 H), 3.04 (dd, J=13.8 and 7.7 Hz, 1 H), 2.41–2.33 (m, 2 H), 1.68 (s, 3 H), 1.68–1.64 (obs m, 1 H), 1.59 (s, 3 H), 1.44 (s, 9 H), 0.93 (d, J=6.6 Hz, 3 H), 0.78 (d, J=6.6 Hz, 3 H); NMR (125 MHz, $CDCl_3$) d 174.87, 153.66, 135.32, 117.91, 78.73, 63.33, 52.19, 43.65, 35.27, 28.31 ($^{13}$C), 25.93, 24.54, 23.70, 22.72, 17.73; high resolution mass spectrum (CI, $NH_3$) m/z 314.2322 [(M+H)$^+$; calculated for $C_{17}H_{32}NO_4$: 314.2331].

B. Boc Protected Amino Ester Derived from D-Phenylalanine

Following the procedure of Example 5A, 1.50 g (60.6 mmol) of the amino ester derived from D-phenylalanine and 1.65 g (75.8 mmol) of di-tert-butyl dicarbonate afforded 1.90 g (90% yield) of the pure Boc-protected amino ester derived from D-phenylalanine after flash chromatography (silica, 10% EtOAc/hexanes): $[\alpha]_D^{24}$ −25.5° (c 1.41, CHCl$_3$); IR (CHCl$_3$) 3425 (W), 2990 (W), 1745 (S), 1710 (S), 1500 (S), 1450 (W), 1370 (m), 1235 (m), 1165 (s), 1075 (m) cm$^{-1}$; $^1$H NMR (500 MHz, CDCl$_3$) d 7.25–7.19 (m, 3 H), 7.06–7.04 (m, 2 H), 5.30 (br s, 1 H), 4.95 (br t, 1 H), 3.74 (s, 3 H), 3.65 (d, J=18.9 Hz, 1 H), 3.16–3.11 (m, 2 H), 2.51 (dd, J=11.6 and 4.5 Hz, 1 H), 1.69 (s, 3 H), 1.61 (s, 3 H), 1.47 (s, 9 H); $^{13}$C NMR (125 MHz, CDCl$_3$) d 173.19, 153.95, 136.54, 135.61, 129.68 (2C), 128.01 (2C), 126.63, 117.70, 78.92, 64.87, 52.17, 40.46, 34.46, 28.30 (3C), 25.92, 17.78; high resolution mass spectrum (CI, methane) m/z 348.2173 [(M+H)$^+$; calculated for C$_{20}$H$_{30}$NO$_4$: 348.2175].

C. Boc Protected Amino Ester Derived from D-Valine

Following the procedure Example 5A, 632 mg (3.17 mmol) of the amino ester derived from D-valine and 864 mg (3.96 mmol) of di-tert-butyl dicarbonate afforded 846 mg (89% yield) of the pure Boc-protected amino ester derived from D-valine after flash chromatography (silica, 10% EtOAc/hexanes): mp 67°–69° C. $[\alpha]_D^{20}$ +13.41° (c 2.26, CHCl$_3$); IR (CHCl$_3$) 3420, 1710, 1490 cm$^{-1}$; $^1$H NMR (500 MHz, CDCl$_3$) d 5.50 (br s, 1 H), 4.93 (br s, 1 H), 3.74 (s, 3 H), 3.12 (br s, 1 H), 2.65 (dd, J=14.4 and 7.0 Hz, 1 H), 2.47 (br s, 1 H), 1.68 (s, 3 H), 1.62 (s, 3 H), 1.44 (s, 9 H), 0.98 (d, J=6.9 Hz, 3 H), 0.92 (d, J=6.9 Hz, 3 H); $^{13}$C NMR (125 MHz, CDCl$_3$) d 173.64, 154.00, 134.77, 118.73, 78.85, 67.05, 52.07, 33.66, 31.04, 28.36 (3C), 26.07, 17.92, 17.85, 17.79; high resolution mass spectrum (CI, methane) m/z 300 2152 [(M+H)$^+$; calculated for C$_{16}$H$_{30}$NO$_4$: 300.2175]. Analysis calculated for C$_{16}$H$_{29}$NO$_4$: C, 64.19; H, 9.76; N, 4.68; found: C, 64.03; H, 9.76; N, 4.68.

EXAMPLE 6

Oxidative Cleavage of a Terminal Olefin to Aldehydic Intermediates

A. Aldehydic Intermediate Derived from D-Leucine

A solution of 7.22 g (23.0 mmol) of N-Boc protected amino ester derived from D-leucine in 100 mL of CH$_2$Cl$_2$ was cooled to −78° C. Ozone was then bubbled into the solution until a blue color appeared. The solution was purged with argon then 6.03 g (23.0 mmol) of triphenylphosphine was added and the solution was allowed to warm to room temperature. The solution was concentrated under reduced pressure and the resulting oil was subjected to chromatography (silica, 20% EtOAc/hexanes) to provide 6.40 g (97% yield) of pure aldehyde derived from D-leucine as a clear colorless oil: $[\alpha]_D^{20}$ −4.12° (c 16.7, CHCl$_3$); IR (CHCl$_3$) 3600, 3410, 1720, 1500 cm$^{-1}$; $^1$H NMR (500 MHz, CDCl$_3$) d 9.64 (s, 1 H), 5.77 (br s, 1 H), 3.77 (s, 3 H), 3.69 (br d, J=17.5 Hz, 1 H), 2.90 (d, J=17.6 Hz, 1 H), 2.34 (d, J=10.4 Hz, 1 H), 1.62–1.52 (m, 2 H), 1.42 (s, 9 H), 0.92 (d, J=6.5 Hz, 3 H), 0.81 (d, J=6.5 Hz, 3 H); $^{13}$C NMR (125 MHz, CDCl$_3$) d 199.29, 173.50, 153.87, 79.51, 59.36, 52.71, 49.71, 43.97, 28.22 (3C), 23.86, 23.56, 23.23; high resolution mass spectrum (CI, methane) m/z 288.1812 [(M+H)$^+$; calculated for C$_{14}$H$_{26}$NO$_5$: 288.1811].

B. Aldehydic Intermediate Derived from D-Phenylalanine

Following the procedure of Example 6A, 5.27 g (15.2 mmol) of N-Boc protected disubstituted amino ester derived from D-phenylalanine provided 3.78 g (78% yield) of pure aldehyde derived from D-phenylalanine which solidified on standing after flash chromatography (silica, 10% EtOAc/hexanes): mp 73°–75° C.; $[\alpha]_D^{24}$ −72.5° (c 1.00, CHCl$_3$); IR (CHCl$_3$) 3420 (w), 3000 (w), 1750 (s), 1735 (s), 1710 (s), 1500 (s), 1210 (s), 1170 (s), 1080 (m), 1060 (m), 725 (s) cm$^{-1}$; $^1$H NMR (500 MHz, CDCl$_3$) d 9.68 (s, 1 H), 7.29–7.25 (m, 3H); 7.02–7.00 (m, 2H); 5.54 (br s, 1 H), 3.84 (d, J=18.4 Hz, 1 H), 3.74 (s, 3 H), 3.61 (d, J=13.3 Hz, 1 H), 3.07 (d, J=17.7 Hz, 1 H), 2.98 (d, J=13.4 Hz, 1 H), 1.45 (s, 9 H); $^{13}$C NMR (125 MHz, CDCl$_3$) d 199.03, 172.11, 154.13, 134.80, 129.72 (2C), 128.25 (2C), 127.22, 79.73, 60.80, 52.71, 48.70, 41.39, 28.27 (3C); high resolution mass spectrum (CI, NH$_3$) m/z 322.1634 [(M+H)$^+$; calculated for C$_{17}$H$_{24}$NO$_5$: 322.1654]. Analysis calculated for C$_{17}$H$_{23}$NO$_5$: C, 63.54; H, 7.21; N, 4.36; found: C, 63.58; H, 7.11; N, 4.28.

C. Aldehydic Intermediate Derived from D-Valine

Following the procedure of Example 6A, 302 mg (1.09 mmol) of N-Boc protected disubstituted amino ester derived from D-valine provided 227 mg (76% yield) of pure aldehyde derived from D-valine after flash chromatography (silica, 10% EtOAc/hexanes): $[\alpha]_D^{20}$ −4.79° (c 2.65, CHCl$_3$); IR (CHCl$_3$) 3600, 3420, 1720, 1490 cm$^{-1}$; $^1$H NMR (500 MHz, CDCl$_3$) d 9.70 (br s, 1 H), 5.60 (br s, 1 H), 3.77 (s, 3 H), 3.68 (m, 1 H), 3.06 (d, J=17.6 Hz, 1 H), 2.32 (m, 1 S), 1.41 (m, 11 H), 0.92 (m, 6 H); $^{13}$C NMR (125 MHz, CDCl$_3$) d 199.67, 172.31, 154.47, 79.71, 63.07, 52.52, 46.18, 34.62, 28.24 (3C), 17.42, 17.23; high resolution mass spectrum (CI, methane) m/z 274.1622 [(M+H)$^+$; calculated for C$_{13}$H$_{24}$NO$_5$: 274.1654]. Analysis calculated for C$_{13}$H$_{23}$NO$_5$: C, 57.13; H, 8.48; N, 5.13; found: C, 57.21; H, 8.69; N, 4.93.

EXAMPLE 7

Carboxylic Acid Intermediate Derived from D-Phenylalanine

A solution of 650 mg (2.02 mmol) of aldehyde derived from D-phenylalanine in 5 mL of DMF was treated with 1.90 g (5.06 mmol) of pyridinium dichromate (PDC) and allowed to stir for 20 h. After this time 80 mL of H$_2$O was added to the mixture followed by extraction with Et$_2$O (3×25 mL). The combined organic extracts were then dried over MgSO$_4$, filtered, and concentrated under reduced pressure to afford a residue. The crude reside was redissolved in 25 mL of Et$_2$O and extracted with a saturated aqueous NaHCO$_3$ solution (3×25 mL) which were then acidified by the addition of a 1N HCl solution. The acidic solution was extracted with Et$_2$O (3×200 mL), dried over MgSO$_4$, filtered, and concentrated under reduced pressure to afford 617 mg the acid derived from D-phenylalanine (90% yield): mp 105°–107° C.; $[\alpha]_D^{26}$ −69.1° (c 1.13, CHCl$_3$); IR (CHCl$_3$) 3240 (w), 2980 (w), 1750 (s), 1720 (s), 1680 (m), 1495 (s), 1165 (s) cm$^{-1}$; $^1$H NMR (500 MHz, CDCl$_3$) d 7.27–7.23 (m, 3H); 7.05–7.00 (m, 2H); 5.58 (br s, 1 H), 3.77–3.70 (m, 4 H), 3.67 (d, J=12.9 Hz, 1 H), 3.06 (d, J=16.2 Hz, 1 H), 3.00 (d, J=13.4 Hz, 1 H), 1.47 (s, 9 H); $^{13}$C NMR (125 MHz, CDCl$_3$) d 175.74, 171.93, 154.14, 135,082, 129.76 (2C), 128.21 (2C), 127.17, 79.78, 61.97, 52.72, 40.96, 39.98, 28.30 (3C); high resolution mass spectrum (CI, methane) m/z 338.1633 [(M+H)$^+$; calculated for C$_{17}$H$_{24}$NO$_6$: 338.1603]. Analysis calculated for C$_{17}$H$_{23}$NO$_6$: C, 60.52; H, 6.87; N, 4.15; found: C, 60.81; H, 7.06; N, 3.94.

EXAMPLE 8

Methyl Ester Intermediate Derived from D-Phenylalanine

A solution of 80.0 mg (0.237 mmol) of carboxylic acid derived from D-phenylalanine in Et$_2$O at 0° C. was treated with a solution of diazomethane (ca. xx mM) till a yellow color persisted. The resulting solution was allowed to evaporate and the residue chromatographed (silica, 75% EtOAc/hexanes) to afford 73.2 mg (92% yield) of ester derived from D-phenylalanine: mp 105°–107° C.; [α]$_D^{26}$–61° (c 0.85, CHCl$_3$); IR (CHCl3) 3420 (s), 3040 (s), 2980 (s), 2960 (s), 1740 (s), 1710 (s), 1500 (s), 1440 (s), 1370 (s), 1240 (s), 1160 (S) 1080 (S) 1045 (m), 1030 (m), 700 (m) cm$^{-1}$; $^1$H NMR (500 MHz, CDCl$_3$) d 7.26–7.22 (m, 3 H), 7.04–7.02 (m, 2 H), 5.58 (br s, 1 H), 3.75 (s, 3 H), 3.68–3.63 (m, 5 H), 3.01 (d, J=16.0, 2 H), 1.46 (s, 9 H); $^{13}$C NMR (62.5 MHz, CDCl$_3$) d 172.10, 170.74, 154.03, 135.23, 129.72 (2C), 128.14 (2C), 127.06, 79.46, 62.16, 52.65, 51.67, 40.79, 40.10, 28.27 (3C); high resolution mass spectrum (CI, methane) m/z 352.1760 [(M+H)$^+$; calculated for C$_{18}$H$_{26}$NO$_6$: 352.1760]. Analysis calculated for C$_{18}$H$_{25}$NO$_6$: 352.1760]. Analysis calculated for C$_{18}$H$_{25}$NO$_6$: C, 61.53; H, 7.17; N, 3.99; found: C, 61.24; H, 7.22; N, 3.90.

EXAMPLE 9

Morpholino Intermediate Derived from D-Phenylalanine

A solution of 100 mg (0.296 mmol) of carboxylic acid derived from D-phenylalanine in 10 mL of THF at –8° C. was treated with 39.0 mg (0.385 mmol) of N-methylmorpholine followed by 54.7 mg (0.400 mmol) of isobutylchloroformate. After stirring for 5 min 34.8 mg (0.400 mmol) of morpholine was added and the reaction mixture allowed to warm to room temperature. After 15 min at room temperature, 50 mL of Et$_2$O was added and the mixture dried over MgSO$_4$, filtered, and concentrated under reduced pressure to afford a residue which was chromatographed (silica, gradient elution 30→100%: EtOAc/hexanes) to provide 112.8 mg (94% yield) of the morpholino amide derived from D-phenylalanine: [α]$_D^{24}$–95° (c 0.85, CHCl$_3$); IR (CHCl$_3$) 3495 (w), 3000 (s), 2980 (w), 1745 (m), 1700 (s), 1635 (m), 1495 (s), 1445 (m), 1230 (m), 1165 (m), 1115 (m), 1075 (w), 1045 (m), 1025 (w) cm$^{-1}$; $^1$H NMR (500 MHz, CDCl$_3$) d 7.27–7.22 (m, 3 H), 7.04–7.02 (m, 2 H), 5.71 (s, 1 H), 3.91 (d, J=15.3 Hz, 1 H), 3.75 (s, 3 H), 3.69–3.57 (m, H), 3.50–3.46 (m, 2 H), 3.01 (d, J=13.3 Hz, 1 H), 2.91 (d, J=15.5 Hz, 1 H), 1.46 (s, 9 H); NMR (62.5 MHz, CDCl$_3$) d 172.37, 168.08, 154.19, 135.20, 129.57 (2C), 127.97 (2C), 126.88, 79.18, 66.68, 66.54, 62.44, 52.41, 46.11, 41.81, 40.92, 38.12, 28.20 (3C); high resolution mass spectrum (CI, methane) m/z 407.2123 [(M+H)$^+$; calculated for C$_{21}$H$_{31}$N$_2$O$_6$: 407.2182].

EXAMPLE 10

Morpholino Intermediate Derived from D-Phenylalanine

A solution of 310 mg (0.763 mmol) of morpholino-amide derived from D-phenylalanine in 5 mL of CH$_2$Cl$_2$ at 0° C. was treated with 164 mg (1.53 mmol) of 2,6-lutidine followed by 339 mg (1.53 mmol) of trimethylsilyltrifluoroacetate (TMSOTf). The resulting mixture was allowed to warm to room temperature and stirred for 15 min. After this time the reaction mixture was treated with 25 mL of CH$_2$Cl$_2$ and 25 mL of a saturated aqueous NaHCO$_3$ solution. The organic portion was further extracted with a saturated aqueous NaHCO$_3$ solution (2×25 mL). The organic portion was then dried over MgSO$_4$, filtered, and concentrated under reduced pressure to afford a residue which crystallized from Et$_2$O to provide 213.5 mg (91% yield) of amine deprotected amine derived from phenylalamine: mp 126°–127° C.; [α]$_D^{22}$+45.5° (C 1.00, CHCl$_3$); IR (CHCl$_3$) 3380 (w), 3000 (m), 1725 (s), 1645 (s), 1595 (m), 1450 (s), 1440 (s), 1230 (s), 1150 (s) cm$^{-1}$; $^1$H NMR (500 MHz, CDCl$_3$) d 7.32–7.27 (m, 3 H), 7.13–7.11 (m, 2 H), 3.68–3.65 (m, 4 H), 3.64 (s, 3 H), 3.57–3.55 (m, 2 H), 3.44–3.42 (m, 2 H), 3.11 (d, J=16.3 Hz, 1 H), 3.02 (d, J=13.1 Hz, 1 H), 2.84 (d, J=13.1 Hz, 1 H), 2.57 (d, J=16.3 Hz, 1 H), 2.01 (br s, 2 H); $^{13}$C NMR (62.5 MHz, CDCl$_3$) d 176.64, 168.87, 135.10, 129.88, (2C), 128.37 (2C), 127.23, 66.73, 66.32, 60.27, 52.08, 46.15, 5.63, 42.88, 41.66; high resolution mass spectrum (CI, HN$_3$) m/z 307.1625 [(M+H)$^+$; calculated for C$_{16}$H$_{23}$N$_2$O$_4$: 307.1658].

EXAMPLE 11

[5(S)-prenyl-(5-benzyl)pyrnolin-4-one-3]-[5(S) -(5-isobutyl)pyrnoline-4-one-3]-(1RR)- cyclohexylmethyl)-2(R),3(S) -dihydroxy5-ethyl-hexane

A. Phe-Leu-Boc Derivative, [5-(S)-prenyl-(5-benzyl)pyrnolin-4-one-3]-2(S)- Boramine-(2-isobutyl) acetate methylestor A solution of 1.00 g (4.04 mmol) of the amine derived from D-phenylalanine in 20 mL of dry toluene was treated with a 20 mL toluene solution of 1.28 g (4.45 mmol) of the aldehyde derived from D-leucine. The toluene was removed under reduced pressure and the residue then chased with additional toluene (3×50 mL). The resulting oil was dissolved in 40 mL of THF and 28.2 mL (14.1 mmol) of a 0.5M solution of KHMDS in toluene added. The resulting solution was allowed to stir for 10 min then quenched by the addition of 200 mL of EtOAc and 200 mL of a 10% aqueous NaHSO$_4$ solution. The organic extract was then washed with a 10% aqueous NaHSO$_4$ solution (2×100 mL) followed by a saturated aqueous NaHCO$_3$ solution (2×100 mL). The organic phase was dried over anhydrous MgSO$_4$ and concentrated under reduced pressure to afford an oil. Flash chromatography (silica, 30% EtOAc/hexanes) provided 1.31 g (67% yield) of product as a glassy solid which could be crystallized from an EtOAc/hexanes mixture at 0° C.: mp 143°–144° C.; [α]$_D^{24}$+28.4° (c 0.87, CHCl$_3$); IR (CHCl$_3$) 3475 (w), 3410 (w), 2980 (w), 1730 (s), 1710 (s), 1650 (m), 1585 (w), 1490 (s), 1170 (s) cm$^{-1}$; $^1$H NMR (500 MHz, CDCl$_3$) d 7.85 (br d, J=3.3 Hz, 1 H), 7.26–7.08 (m, 6 H), 6.13 (br s, 1 H), 5.01 (t, J=7.2 Hz, $^1$H), 3.56 (s, 3 H), 2.99 (d, J=13.6 Hz, 1 H), 2.85 (d, J=13.6 Hz, 1 H), 2.46–2.30 (m, 2 H), 2.18–0.97 (m, 2 H), 1.70–1.45 (m, 1 H), 1.66 (s, 3 H), 1.40 (s, 9 H), 0.92–0.75 (m, 6 H); $^{13}$C NMR (125 MHz, CDCl$_3$) d 200.98, 173.70, 162.03, 154.42, 136.03, 135.36, 129.94 (2C), 127.85 (2C), 126.59, 116.93, 110.83, 78.78, 71.15, 59.85, 52.37, 42.26, 41.77, 34.84, 28.34 (3C), 25.82, 24.32, 24.14, 23.45, 18.02; high resolution mass spectrum (CI, NH$_3$) m/z 485.3038 [(M+H)$^+$; calculated for C$_{28}$H$_{41}$N$_2$5: 485.3015]. Analysis calculated for C$_{28}$H$_{40}$N2O$_5$: C, 69.39; H, 8.32; N, 5.78; found: C, 69.10; H, 8.46; N, 5.68.

B. Phe-Leu-NH₂, [5 (S) -prenyl-(5-abenzyl) pyrrolinone-4-one-3]-2(S)-amino-(2-isobutyl) acetate methylester A solution of 300 mg (0.619 mmol) of the Phe-Leu-Boc pyrrolinone in 5.0 mL of $CH_2Cl_2$ was treated at 0° C. with 331 mg (1.48 mmol) of TMSOTf. The reaction mixture was allowed to warm to room temperature and stirred for 15 min, after which time the mixture was quenched by the addition of 25 mL of $CH_2Cl_2$ followed by 100 mL of a saturated aqueous $NaHCO_3$ solution. The organic layer was then washed with a further 100 mL of aqueous $NaHCO_3$ solution, dried over anhydrous $MgSO_4$ and concentrated to afford a crude oil. Flash chromatography of the residue (silica, 80% EtOAc/hexanes) provided 201 mg (84% yield) of the free amino ester as a light yellow oil: $[\alpha]_D^{20}$+15.9° (c 7.68, $CHCl_3$); IR ($CHCl_3$) 3440 (m), 3300 (w), 2980 (s), 1730 (s), 1650 (s), 1560 (s), 1440 (m), 1220 (m), 1160 (m) cm$^{-1}$; $^1$H NMR (500 MHz, $CDCl_3$) d 7.80 (d, J=4.0 Hz, 1 H), 7.30–7.08 (m, 5 H), 5.68 (br d, J=3.5 Hz, 1 H), 5.03 (m, 3 H), 2.96 (d, J=13.5 Hz, 1 H), 2.84 (d, J=13.5 Hz, 1 H), 2.40 (dd, J=14.6 and 7.3 Hz, 1 H), 2.32 (dd, J=14.5 and 7.4 Hz, 1 H), 2.13 (br s, 2 H), 1.82–1.55 (m, 3 H), 1.68 (s, 3 H), 1.58 (s, 3 H), 0.89 (d, J=6.6 Hz, 3 H), 0.81 (d, J=6.6 Hz, 3 H); $^{13}$C NMR (125 MHz, $CDCl_3$) d 201.74, 175.99, 160.13, 135.78, 135.58, 130.00 (2C), 127.83 (2C), 126.59, 117.12, 115.56, 70.76, 58.37, 52.06, 46.81, 41.60, 34.77, 25.83, 24.60, 23.92, 22.95, 18.04; high resolution mass spectrum (CI, $NH_3$) m/z 384.2393 [M$^+$; calculated for $C_{23}H_{32}N_2O_3$: 384.2413]. Analysis calculated for $C_{23}H_{32}N_2O_3$: C, 71.84; H, 8.39; N: 7.29; found: C, 71.69; H, 8.56; N, 7.45.

C. Phe-Leu-bis-silyl isostere

A solution of 92.0 mg (0.239 mmol) of the Phe-Leu amine in 5 mL of dry toluene was treated with a 5 mL toluene solution of 120 g (0.239 mmol) of the Abbott aldehyde. The toluene was removed under reduced pressure and the residue was chased with additional toluene (3×5 mL). The resulting oil was then dissolved in 4.0 mL of THF and 1.90 mL (0.956 mmol) of a 0.5M solution of KHMDS in toluene added. The resulting solution was allowed to stir for 10 min then quenched by the addition of 10 mL of EtOAc and 10 mL of a 10% aqueous $NaHSO_4$ solution. The organic extract was then washed with a 10% aqueous $NaHSO_4$ solution (2×10 mL) followed by a saturated aqueous $NaHCO_3$ solution (2×10 mL). The organic phase was dried over anhydrous $MgSO_4$ and concentrated under reduced pressure to afford an oil. Flash chromatography (silica, 20% EtOAc/hexanes) provided 96.0 g (48% yield) of product as an oil: $[\alpha]_D^{25}$– 152° (C 0.73, $CHCl_3$); IR ($CHCl_3$) 3460 (m), 2980 (s), 2960 (s), 1650 (s), 1580 (s), 1450 (m), 1255 (m), 1155 (m), 1080 (m), 840 (s) cm$^{-1}$; $^1$H NMR (500 MHz, $CDCl_3$) d 8.09 (d, J=4.0 Hz, 1 H), 7.85 (d, J=3.7 Hz, 1 H), 7.22–7.18 (m, 3 H), 7.08–7.06 (m, 2 H), 6.99 (d, J=3.5 Hz, 1 H), 5.50 (d, J=3.9 Hz, 1 H), 4.91 (t, J=7.2 Hz, 1 H), 3.79 (s, 1 H), 3.63 (d, J=10.2 Hz, 1 H), 2.81 (d, J=13.5 Hz, 1 H), 2.74 (d, J=13.5 Hz, 1 H), 2.69–2.65 (m, 1 H), 2.47 (dd, J=14.5 and 7.6 Hz, 1 H), 2.24 (dd, J=14.5 and 6.9 Hz, 1 H), 1.80 (br d, J=12.4 Hz, 1 H), 1.75 (dd, J=13.9 and 4.7 Hz, 1 H), 1.70–1.55 (m, 12 H), 1.46–1.38 (m, 2 H), 1.31–1.23 (m, 3 H), 1.15–1.04 (m, 2 H), 1.00–0.76 (m, 34 H), 0.15 (s, 3 H), 0.08 (s, 3 H), 0.08 (s, 3 H), 0.04 (s, 3 H); $^{13}$C NMR (125 MHz, $CDCl_3$) d 203.25, 202.60, 163.46, 160.45, 135.91, 135.55, 129.96 (2C), 128.13 (2C), 127.02, 116.74, 112.16, 110.60, 80.62, 75.00, 70.73, 67.38, 47.96, 42.23, 41.86, 41.54, 35.19, 34.58, 33.91, 33.66, 32.81, 26.71, 26.66, 26.54, 26.33 (3C), 26.15 (3C), 25.82, 24.87, 24.45, 24.17, 23.61, 21.45, 18.52, 18.19, 18.09, –3.41, –3.45, –4.51, –4.68; high resolution mass spectrum (CI, $NH_3$) m/z 833.6002 [(M+H)$^+$; calculated for $C_{50}H_{85}N_2O_4Si_2$: 833.6048]; m/z 831.5892 [(M—H); calculated for $C_{50}H_{83}N_2O_4Si_2$: 831.5892].

D. Phe-Leu-bis-hydroxy isostere, structure (7)

A solution of 10.0 mg of Phe-Leu-bis-silyl isostere in a 3:1:1 mixture of $HOAc:H_2O:THF$ was warmed at 50° C. for 5 h. The reaction was then concentrated to a solid under reduced pressure and the residue chromatographed (silica, gradient elution 20→70%: EtOAc/hexanes) to provide 4.5 mg (62% yield) of product as a solid which was crystallized from an EtOAc/hexanes mixture at 0° C.; mp 187°–188° C.: $[\alpha]_D^{23}$–242° (c 0.636, $CHCl_3$); IR ($CHCl_3$) 3460 (m), 3360 (m), 2940 (s), 1650 (m), 1580 (s), 1450 (m), 1160 (m) cm$^{-1}$; $^1$H NMR (500 MHz, $CDCl_3$) d 7.97 (d, J=3.6 Hz, 1 H), 7.71 (d, J=3.6 Hz, 1 H), 7.22–7.17 (m, 3 H), 7.06–7.05 (m, 2 H), 5.47 (br s, $^1$H), 4.94 (t, J=7.3 Hz, 1 H), 3.38 (br s, 1 H), 3.28 (d, J=7.1 Hz, 1 H), 2.99–2.95 (m, 2 H), 2.82 (s, 2 H), 2.69 (br s, 1 H), 2.49 (dd, J=14.4 and 7.8 Hz, 1 H), 2.28 (dd, J=14.4 and 6.9 Hz, 1 H), 1.88–1.80 (m, 2 H), 1.69–1.30 (m, 18 H), 1.20–1.13 (m, 4 H), 0.93–0.75 (m, 14 H); $^{13}$C NMR (125 MHz, $CDCl_1$) d 204.15, 203.03, 163.85, 159.89, 136.20, 135.32, 129.97 (2C), 127.99 (2C), 126.88, 116.50, 111.28, 110.61, 77.11, 71.30, 71.16, 68.67, 46.82, 42.98, 42.04, 38.44, 34.76, 34.05, 33.42, 33.29, 31.83, 26.64, 26.32, 25.87, 24.94, 24.47, 24.28, 24.05, 23.98, 21.46, 18.13; high resolution mass spectrum (CI, $NH_3$) m/z 605.4371 [(M+H)$^+$; calculated for $C_{38}H_{57}N_2O_4$: 605.4318].

EXAMPLE 12

[5(S)-prenyl-(5-benzyl)pyrrolin-4-one-3]-2(R) -isobutylacetate-[1-amino-1(S)-cyclohexylmethyl-2(R)₃3(S)-dihydroxy-5-methyl-hexane]-amide, Structure (10a)

A. Methylvaleric acid substrate, 1-isohexylamide-5(S)-benzyl-oxizolidinane

A solution of 5.00 g (28.2 mmol) of oxazolidinone in 100 mL of THF at –78° C. was treated with 17.6 mL (28.2 mmol) of a 1.6M hexanes solution of n-butyl lithium and allowed to stir for 15 min. After this time 3.80 g (28.2 mmol) of 4-methylvalerylchloride was added and the mixture allowed to stir for 30 min. The mixture was quenched with 50 mL of a saturated aqueous solution of $NaHCO_3$ and 200 mL of $CH_2Cl_2$. The organic layer was washed with a saturated aqueous solution of $NaHCO_3$ (2×50 mL) followed by a saturated aqueous solution of NaCl (2×50 mL). The organic phase was dried over anhydrous $MgSO_4$ and concentrated under reduced pressure to afford an oil. Flash chromatography (silica, 10% EtOAc/hexanes) provided 7.48 g (96% yield) of product as an oil: $[\alpha]_D^{25}$+53.7° (c 1.07, $CHCl_3$); IR ($CHCl_3$) 3030 (w), 2975 (in), 2940 (w), 1790 (s), 1705 (s), 1390 (S), 1355 (S), 1230 (In), 1195 (S), 1100 (m) cm$^{-1}$; $^1$H NMR (500 MHz, $CDCl_3$) d; $^{13}$C NMR (125 MHz, $CDCl_3$) d 174.45, 154.28, 136.22, 130.28 (2C), 129.78 (2C), 128.16, 66.97, 55.98, 38.74, 34.46, 33.98, 28.51, 23.22 (2C).

B. Prenylated Methylvaleric acid substrate, 1-(2(4)-prenyl-4-methyl-pentamine)amide-S(S)-benzyl-oxizolidinone A solution of 1.0 g (36.3 mmol) of oxazolidinone in 30 mL of THF at –78° C. was treated with 4.36 mL (43.6 mmol) of a 1.0M solution of NaHMDS in THF. The resulting solution was allowed to stir at −78° C. for a further 15 min, after which time 2.16 g (14.5 mmol) of 1-bromo-3-methyl-2-butene was added. The reaction mixture was then allowed to warm to 0° C. and quenched by the addition of 20 mL of EtOAc and 50 mL of a 10% aqueous NaHSO$_4$ solution. The organic extract was then washed with a 10% aqueous NaHSO$_4$ solution (2×50 mL) followed by a saturated aqueous NaHCO$_3$ (50 mL). The organic phase was dried over anhydrous MgSO$_4$ and concentrated under reduced pressure to afford an oil. Chromatography (silica, 10% EtOAc/hexanes) provided 1.12 g (90% yield) of product as an oil: $[\alpha]_D^{26}$+50.2° (c 1.11, CHCl$_3$); IR (CHCl$_3$) 2960 (m), 1780 (S), 1695 (S), 1455 (m), 1385 (s), 1350 (s), 1195 (s), 1100 (s), 905 (m) cm$^{-1}$; $^1$H NMR (500 MHz, CDCl$_3$) d 7.35–7.31 (m, 2 H), 7.28 (d, J=7.4 Hz, 1 H), 7.23–7.21 (m, 2 H), 5.18 (td, J=6.8 and 1.2 Hz, 1 H), 4.70–4.65 (m, 1 H), 4.18–4.11 (m, 2 H), 4.03–3.97 (m, 1 H), 3.25 (dd, J=13.3 and 3.3 Hz, 1 H), 2.64 (dd, J=13.3 and 9.9 Hz, 1 H), 2.43–2.37 (m, 1 H), 2.26–2.21 (m, 1 H), 1.74–1.70 (m, 1 H), 1.69 (s, 3 H), 1.62 (s, 3 H), 1.60–1.53 (m, 1 H), 1.34–1.29 (m, 1 H), 0.89 (dd, J=7.1 Hz, 6 H), $^{13}$C NMR (62.5 MHz, CDCl$_3$) d 176.71, 152.94, 135.41, 133.59, 129.27 (2C), 128.79 (2C), 127.14, 120.92, 65.64, 55.24, 40.74, 40.61, 37.76, 31.68, 26.22, 26.10, 25.71, 22.80, 22.48, 17.73; high resolution mass spectrum (CI, methane) m/z 344.2192 [(M+H)$^+$; calculated for C$_{21}$H$_{30}$NO$_3$: 344.2225].

C. Prenylated alcohol, 2 (R) -pronyl-4-methyl-pentanol

A solution of 6.16 g of alkylated oxazolidinone in 300 mL of THF at 0° C. was treated with a solution of benzyl mercaptide which was formed at 0° C. by the addition of 16.8 mL (26.90 mmol) of a 1.6M solution of n-butyl lithium in hexanes to a 100 mL THF solution containing 4.46 g (35.87 mmol) of benzyl mercaptan. The resulting mixture was allowed to stir for 15 rain after which time 1.02 g (26.90 mmol) of LAH was added. After 15 min the reaction mixture was quenched by the addition of 1.0 mL of H$_2$O, then 1.0 mL of 15% aqueous NaOH, and 3.0 mL of H$_2$O. The mixture was stirred for a further 30 min, filtered, and the filter cake itself washed thoroughly with THF (3×250 mL) and ethyl ether (3×250 mL). The organic extracts were concentrated under reduced pressure to afford an oil. Chromatography (silica, 10% EtOAc/hexanes) provided 2.76 g (90% yield) of product as an oil: $[\alpha]_D^{22}$−9.84° (c 1.25, CHCl$_3$); IR (CHCl$_3$) 3620 (w), 3480 (br, w), 2980 (s), 1470 (m), 1380 (m), 1020 (m) cm$^{-1}$; $^1$H NMR (500 MHz, CDCl$_3$) d 5.16 (td, J=7.2 Hz, I H), 3.52–3.50 (m, 2 H), 2.02 (t, J= 6.9 Hz, 1 H), 1.71 (s, 3 H), 1.69–1.59 (m, 6 H), 1.36–1.15 (m, 1 H), 1.13–0.91 (m, 1 H), 0.89 (d, J=6.6 Hz, 3 H), 0.88 (d, J=6.6 Hz, 3 H); $^{13}$C NMR (62.5 MHZ, CDCl$_3$) d 132.56, 122.55, 65.86, 40.40, 38.74, 29.87, 25.72, 25.26, 22.89, 22.71, 17.68; high resolution mass spectrum (CI, methane) m/z 170.1663 [M$^+$; calculated for C$_{11}$H$_{22}$O: 170.1671], m/z 171.1758 [(M+H)$^+$; calculated for C$_{11}$H$_{23}$O: 171.1749]. Analysis calculated for C$_{11}$H$_{22}$O: C, 77.58; H, 13.02; found: C, 77.29; H, 13.23.

D. Prenylated TBDMS protected alcohol, 2(R)-prenyl-4-methyl-1-tertbutyldimetholsilanol-pentane A solution of 1.00 g (5.87 mmol) of alcohol in 10 mL of DMF was treated with 999 mg (14.7 mmol) of imidazole and 1.06 g (7.05 mmol) of TBSCl. The reaction mixture was allowed to stir for 16 h and 250 mL of H$_2$O and 50 mL of Et$_2$O added. The organic layer was concentrated under reduced pressure to afford an oil. Chromatography (silica, 2% EtOAc/hexanes) provided 1.65 g (99% yield) of product as an oil: $[\alpha]_D^{22}$+0.92° (c 1.30, CHCl$_3$); IR (CHCl$_3$) 2980 (s), 1470 (w), 1255 (m), 1090 (s), 835 (s) cm$^{-1}$; $^1$H NMR (500 MHz, CDCl$_3$) d 5.12 (t, J=7.2 HZ, 1 H), 3.47–3.41 (m, 2 H), 2.07–2.02 (m, 1 H), 1.94–1.89 (m, 1 H), 1.70 (s, 3 H), 1.67–1.61 (m, 1 H), 1.60 (s, 3 H), 1.58–1.53 (m, 1 H), 1.21–1.16 (m, 1 H), 1.08–1.02 (m, 1 H), 0.90 (s, 9 H), 0.87 (d, J=6.6 Hz, 3 H), 0.86 (d, J=6.5 Hz, 3 H), 0.03 (s, 6 H); $^{13}$C NMR (62.5 MHz, CDCl$_3$) d 131.97, 123.11, 65.44, 40.63, 39.04, 29.84, 25.98 (3C), 25.87, 25.45, 23.10, 22.99, 18.33, 17.83, −5.40 (2C); high resolution mass spectrum (CI, NH$_3$) m/z 285.2591 [(M+H)$^+$; calculated for C$_{17}$H$_{37}$OSi: 285.2613]. Analysis calculated for C$_{17}$H$_{36}$OSi: C, 71.76; H, 12.75; found: C, 71.85; H, 13.02.

E. Aldehyde amino acid equivalent, 3(R)-tert-butyldimethnol silyl hydroxymethyl)-5-methyl-hexan-1-al A solution of 2.50 g (8.79 mmol) of olefin in 100 mL of CH$_2$Cl$_2$ was cooled to −78° C. and ozone bubbled trough the solution until a blue color appeared. The solution was then treated with 7.5 mL of dimethylsulphide and the solution allowed to warm to room temperature. The solution was concentrated under reduced pressure and the resulting oil was subjected to chromatography (silica, 5% EtOAc/hexanes) to provide 1.52 g (85% yield) of aldehyde as an oil: $[\alpha]_D^{22}$+12.1° (c 0.91, CHCl$_3$); IR (CHCl$_3$) 2980 (s), 2740 (w), 1730 (s), 1470 (m), 1390 (w), 1255 (m), 1095 (s), 340 (s) cm$^{-1}$; $^1$H NMR (500 MHz, CDCl$_3$) d 9.77 (dd, J=2.7 and 1.9 Hz, 1 H), 3.62 (dd, J =9.9 and 4.4 Hz, 1 H), 3.39 (dd, J=9.8 and 7.3 Hz, 1 H), 2.43 (ddd, J=16.1, 7.6, and 2.8 Hz, 1 H), 2.29 (ddd, J= 16.1, 5.3, and 1.9 Hz, 1 H), 2.25–2.21 (m, 1 H), 1.63–1.58 (m, 1 H), 1.25–1.20 (m, 1 H), 1.11–1.05 (m, $^1$H), 0.91 (d, J=6.6 Hz, 3 H), 0.89–0.87 (m, 12 H), 0.03 (s, 6 H); $^{13}$C NMR (62.5 MHz, CDCl$_3$) d 202.75, 65.98, 47.03, 40.51, 34.30, 25.81 (3C), 25.22, 22.71, 22.66, 18.19, −5.61 (2C); high resolution mass spectrum (CI, NH$_2$) m/z 259.2114 [(M+H)$^+$; calculated for C$_{14}$H$_{31}$O$_2$Si: 259.2093].

F. Phe-"Leu" TBDMS protected alcohol, [5 (8) -(5-benzyl) yrrolin-4-one-3]-2(S) -isobutyl-tert butyl dimethyl silylethlether A solution of 1.00 g (4.04 mmol) of the amine derived from D-phenylalanine in 25 mL of dry toluene was treated with a 25 mL toluene solution of 1.10 g (4.25 mmol) of aldehyde. The toluene was removed under reduced pressure and the residue then chased with additional toluene (3×50 mL). The resulting oil was dissolved in 30 mL of THF and 24.2 mL (12.1 mmol) of a 0.5M solution of KHMDS in toluene added. The resulting solution was allowed to stir for 10 min then quenched by the addition of 50 mL of EtOAc and 50 mL of a 10% aqueous NaHSO$_4$ solution. The organic extract was then washed with a 10% aqueous NaHSO$_4$ solution (2×50 mL) followed by a saturated aqueous NaHCO$_3$ solution (2×50 mL). The organic phase was dried over anhydrous MgSO$_4$ and concentrated under reduced pressure to afford an oil. Flash chromatography (silica, 10→20% gradient elution: EtOAc/hexanes) provided 75.6 mg (73% yield) of product as a colorless solid: mp 126°–127° C.; $[\alpha]_D^{22}$−17° (c 0.80, CHCl$_3$); IR (CHCl$_3$) 3450 (w), 2960 (s), 1660 835 (s), 1530 (s), 1470 (w), 1330 (w), 1255 (m), 1155 (w), 1090 (s), 835 (s) cm$^{-1}$; $^1$H NMR (500 MHz, CDCl$_3$) d 7.58 (d, J=3.8 Hz, 1 H), 7.20–7.16 (m, 3 H), 7.12–7.10 (m, 2 H), 4.96–4.92 (m, 2 H), 3.40 (dd, J=9.6 and 4.2 Hz, 1 H), 3.11 (dd, J= 9.6 and 6.0 Hz, 1 H), 2.93 (d, J=13.4 Hz, 1 H), 2.81 (dd, J=13.4 Hz, 1 H), 2.54–2.51 (m, 1 H), 2.41 (dd, J=14.4 and 7.3 Hz, 1 H), 2.28 (dd, J=14.5 and 7.4 Hz, 1 H), 1.63 (s, 3 H), 1.56 (s, 3 S), 1.31–1.27 (m, 3 S), 0.84 (s, 9 H), 0.81 (d, J=6.0 Hz, 3 H), 0.78 (d, J=6.0 Hz, 3 H), −0.02 (s, 3 H), −0.05 (s, 3 H) ; $^{13}$C NMR (62.5 MHz, CDCl$_3$) d 203.41, 161.12, 135.87, 135.38, 130.04 (2C), 127.79 (2C), 126.55, 117.48, 115.42, 69.97, 65.95, 42.09, 40.24, 34.72, 33.24, 25.89 (3C), 25.81, 25.36, 23.72, 21.81, 18.20, 18.02, −5.43 (2C); high resolution mass spectrum (CI, NH$_3$) m/z 456.3265 [(M+H)$^+$; calculated for C$_{28}$H$_{46}$NO$_2$Si: 456.3298]. Analysis calculated for C$_{28}$H$_{45}$NO$_2$Si: C, 73.79; H, 9.95; N,3.07; found: C, 73.77; H, 10.05; N, 3.01.

G. Phe-"Leu" alcohol, [5 (S)-prenyl-(5-benzl)pyrrolin-4-owe-3]-2-(R)-isobutyl-ethanol A solution of 1.15 g (2.52 mmol) of Phe-"Leu"-protected alcohol in 50 mL of a 3:1:1 mixture of HOAc:H$_2$O:THF was stirred for 3 h. The mixture was then concentrated to a solid under reduced pressure and the residue crystallized from benzene/hexanes at 0° C. to provide 820 mg (95% yield) of a colorless crystalline solid: mp 149°–150° C.; [α]$_D^{24}$ −1.90° (c 1.00, CHCl$_3$); IR (CHCl$_3$) 3450 (m), 2960 (s), 1645 (s), 1570 (s), 1450 (m), 1380 (w), 1155 (w) cm$^{-1}$; $^1$H NMR (500 MHz, CDCl$_3$) d 7.51 (d, J=3.7 Hz, 1 H), 7.22–7.19 (m, 3 H), 7.14–7.12 (m, 2 H), 5.19 (br s, 1 H), 5.00 (td, J=7.4 and 1.2 Hz, 1 H), 3.46–3.40 (m, 2 H), 3.04 (d, J=13.3 Hz, 1 H), 2.84 (d, J= 13.4 Hz, 1 H), 2.64 (br t, 1 H), 2.50–2.43 (m, 2 H), 2.36 (dd, J=14.4 and 7.5 Hz, 1 H), 1.68 (s, 3 H), 1.62 (s, 3 H), 1.25–1.18 (m, 3 H), 0.79 (d, J=5.4 Hz, 3 H), 0.77 (d, J=5.4 Hz, 3 H); $^{13}$C NMR (62.5 MHz, CDCl$_3$) d 204.27, 161.74, 136.07, 135.42, 129.96 (2C), 127.84 (2C), 126.75, 117.13, 115.32, 71.03, 65.96, 42.09, 39.27, 35.18, 34.87, 25.89, 24.96, 23.21, 21.94, 18.11; high resolution mass spectrum (CI, NH$_3$) m/z 342.2401 [(M+H)$^+$; calculated for C$_{22}$H$_{32}$NO$_2$: 342.2433]. Analysis calculated for C$_{22}$H$_{31}$NO$_2$: C, 77.38; H, 9.15; N, 4.10; found: C, 77.52; H, 9.25; N, 3.89.

H. O-acetonide N-Boc of Abbott dihydroxy isostere amine, 1-boc-amino-1 (R)-cyclohexylmethy-2(R)]3 (S)-5 dihydroxyacetonide-5 methyl-hexane A solution of 500 mg (1.46 mmol) of the Abbott diol in 10 mL of a 1:1 THF: 2,2-dimethoxylpropane mixture was stirred for 24 h and then concentrated under reduced pressure. The residue was chromatographed (silica, 10→20% gradient elution: EtOAc/hexanes) to afford 534 mg (96% yield) of acetonide; [α]$_D^{24}$ −16.2° (c 1.05, CHCl$_3$); IR (CHCl$_3$) 3450 (m), 2930 (s), 2860 (m), 1710 (s), 1500 (s), 1450 (m), 1370 (s), 1240 (m), 1070 (m), 1035 (m), 910 (m) cm$^{-1}$; $^1$H NMR (500 MHz, CDCl$_3$) d 4.66 (d, J=9.3 Hz, 1 H), [4.42 (br s), minor], 4.25–4.21 (m, 1 H), 3.99 (d, J=6.6 Hz, 1 H), [3.93 (br s), minor], 3.80–3.74 (m, 1 H), [3.65 (br s), minor], 1.95 (d, J =12.5 Hz, 1 H), 1.76–1.62 (m, 6 H), 1.48 (s, 3 H), 1.44 (s, 9 H), 1.35 (s, 3 H), 1.28–1.14 (m, 7 H), 0.94–0.91 (m, 7 H), 0.85–0.79 (m, 1 H); $^{13}$C NMR (62.5 MHz, CDCl$_3$) d 154.95, 107.10, 79.26, 78.75, 75.65, (47.82, minor), 46.75, (43.66, minor), 42.83, 37.81, 33.93, 33.77, (33.48, minor), 32.91, 28.33 (3C), 27.07, 26.52, 26.39, 26.20, 25.52, 24.47, 23.66, 21.54; high resolution mass spectrum (CI, NH$_3$) m/z 384.3083 [(M+H)$^+$; calculated for C$_{22}$H$_{42}$NO$_4$: 384.3 114].

I. O-acetonide of Abbott dihydroxy isostere amine, 1 (S) cyclohexylmethyl-2 (R), 3 (S) dihydroxy acetomide-5 methyl-hexamine A solution of 300 mg (0.782 mmol) of acetonide in 5 mL of CH$_2$Cl$_2$ was treated with 210 mg (1.96 mmol) of 2,6-lutidine followed by 348 mg (1.56 mmol) of TMSOTf. The resulting mixture was stirred for 15 min then treated with 25 mL of Et$_2$O and 25 mL of a saturated aqueous NaHCO$_3$ solution. The organic portion was further washed with a saturated aqueous NaHCO$_3$ solution (2×25 mL). The organic portion was then dried over MgSO$_4$, filtered, and concentrated under reduced pressure to afford a residue which was chromatographed (silica, 50→100% gradient elution: Et$_2$O/hexanes) to afford 184 mg (83% yield) of amine; [α]$_D^{24}$ −49.3° (c 1.10, CHCl$_3$); IR (CHCl$_3$) 2930 (s), 1450 (m), 1380 (m), 1370 (m), 1235 (m), 1050 (m), 870 (m) cm$^{-1}$; $^1$H NMR (500 MHz, CDCl$_3$) d 4.14 (ddd, J= 11.1, 5.6, and 2.7 Hz, 1 H), 3.75 (t, J=6.7 Hz, 1 H), 2.94–2.90 (m, 1 H), 1.87–1.81 (m, 2 H), 1.77–1.64 (m, 4 H), 1.60–1.47 (m, 2 H), 1.45 (s, 3 H), 1.39 (br s, 2 H), 1.45 (s, 3 H), 1.32–1.07 (m, 7 H), 0.96 (d, J=6.8 Hz, 3 H), 0.92 (d, J= 6.5 Hz, 3 H), 0.81 (ddd, J=24.1, 12.2, and 3.2 Hz, 1 H); $^{13}$C NMR (62.5 MHz, CDCl$_3$) d 2107.26, 82.38, 75.12, 47.21, 41.94, 38.25, 34.54, 33.55, 32.21, 28.00, 26.38, 26.18, 25.95, 25.69, 24.42, 23.84, 21.16; high resolution mass spectrum (CI, NH$_3$) m/z 284.2537 [(M+H)$^+$; calculated for C$_{17}$H$_{34}$NO$_2$: 284.2589].

EXAMPLE 13

[5 (S)-prenyl-(5-benzyl) pyrrolin-4-one-3] -5 (S)-(5-isobutyl)pyrrolin-4-one-3-] -(5 (S) −5-isobutyl)Pyrrolin-4-one-3]-(5(S) -(5-isopropyl)pyrrolin-4-one-3]-2(S)-Boc-amino-(2-benzyl) acetate methyl ester, Structure (31 )

(31)

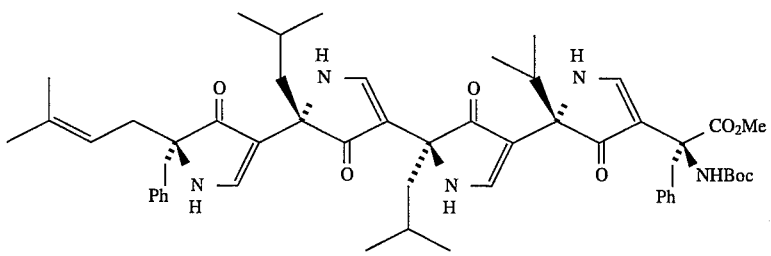

A. Leu-Leu-Boc, [5 (S)-prenyl-(5-isobutyl) pyrolin-4-one-3]-2 (S)-Boc-amino-(2-isobutyl) acetate methyl ester A solution of 1.0 g (4.69 mmol) of the amine derived from D-leucine in 20 mL of dry toluene was treated with a 20 mL toluene solution of 1.41 g (4.92 mmol) of the aldehyde derived from D-leucine. The toluene was removed under vacuum and the residue was chased with additional toluene (3×50 mL). The resulting oil was then dissolved in 75 mL of THF and 32.8 mL (16.4 mmol) of a 0.5M solution of KHMDS in toluene added. The resulting solution was allowed to stir for 10 min then quenched by the addition of 200 mL of EtOAc and 200 mL of a 10% aqueous NaHSO$_4$ solution. The organic extract was then washed with a 10% aqueous NaHSO$_4$ solution (2×100 mL) followed by a saturated aqueous NaHCO$_3$ solution (2×100 mL). The organic phase was dried over anhydrous MgSO$_4$ and concentrated under reduced pressure to afford an oil. Flash chromatography (silica, 30% EtOAc/hexanes) provided 2.36 g (90% yield) of product as a glassy solid; $[\alpha]_D^{24}$ –66.1° (c 1.19, CHCl$_3$); IR (CHCl$_3$) 3450 (w), 3420 (w), 3320 (w); 2970 (S), 1740 (S), 1720 (s), 1650 (m), 1570 (m), 1490 (s), 1370 (m), 1240 (m), 1175 (s) cm$^{-1}$; $^1$H NMR (500 MHz, CDCl$_3$) d; $^{13}$C NMR (125 MHz, CDCl$_3$) d; high resolution mass spectrum (CI, NH$_3$) m/z 451.3142 [(M+H)$^+$; calculated for C$_{25}$H$_{42}$N$_2$O$_5$: 451.3172]. Analysis calculated for C$_{25}$H$_{42}$N$_2$O$_5$: C, 66.64; H, 9.40; N: 6.22 found: C, 66.43; H, 9.06; N, 5.99.

B. Leu-neu-NH$_2$, [5 (S)-prenyl-(5-isobutyl) pyrolin-4-one-3]-2 (S)-amino-(2-isobutyl) acetate methyl ester A solution of 335 mg (0.743 mmol) of the Leu-Leu-Boc pyrrolinone in 5.0 mL of CH$_2$Cl$_2$ was treated at 0° C. with 331 mg (1.49 mmol) of TMSOTf. The reaction mixture was allowed to warm to room temperature and stir for 15 min. The reaction was then quenched by the addition of 25 mL of CH$_2$Cl$_2$ followed by 100 mL of a saturated aqueous NaHCO$_3$ solution. The organic layer was then washed with a further 100 mL of aqueous NaHCO$_3$ solution, dried over anhydrous MgSO$_4$ and concentrated to afford a crude oil. Flash chromatography (silica, 20% EtOAc/hexanes) provided 236 mg (90% yield) of the free amino ester which was crystallized from hexanes/EtOAc at 0° C.: mp 108°–109° C.; $[\alpha]_D^{24}$ –68.4° (c 1.03, CHCl$_3$); IR (CHCl$_3$) 3480 (m), 3400 (w), 2985 (s), 1740 (s), 1660 (s), 1580 (s), 1440 (w), 1230 (m), 1170 (m), 910 (w) cm$^{-1}$; $^1$H H NMR (500 MHz, CDCl$_3$) d 7.95 (d, J=3.5 Hz, 1 H), 5.18 (br s, 1 H), 5.03 (t, J=1.3 Hz, 1 H), 3.67 (s, 3 H), 2.23 (d, J=7.4 Hz, 1 H), 1.80–1.75 (m, 1 H), 1.69 (s, 3 H), 1.65 (dd, J=14.1 and 7.1 Hz, 1 H), 1.60–1.56 (obs m, 1 H), 1.58 (s, 3 H), 1.52 (dd, J=12.5 and 6.4 Hz, 1 H), 0.96 (d, J=6.7 Hz, 3 H), 0.87 (d, J=6.4 Hz, 3 H), 0.86 (d, J=6.5 Hz, 3 H), 0.78 (d, J=6.5 Hz, 3 H); $^{13}$C NMR (125 MHz, CDCl$_3$) d 202.61, 176.26, 159.88, 135.66, 117.50, 115.16, 70.86, 58.29, 51.99, 46.79, 44.02, 36.47, 25.87, 24.71, 24.34, 24.21, 23.86, 23.63, 23.01, 18.08; high resolution mass spectrum (CI, methane) m/z 351.2612 [M$^+$; calculated for C$_{20}$H$_{35}$N$_2$O$_3$: 351.2647]. Analysis calculated for C$_{20}$H$_{34}$N$_2$O$_3$: C, 68.54; H, 9.78, N, 7.99; found: C, 68.61; H, 9.65; N, 7.75.

C. Val-Phe-Boc, [5 (S)-prenyl-(5-isopropyl) pyrolin-4-one-3 ]-2 (S)-Boc-amino-(2-benzyl) acetate methyl ester A solution of 886 mg (4.45 mmol) of the amine derived from D-valine in 25 mL of dry toluene was treated with a 25 mL toluene solution of 1.50 g (4.67 mmol) of the aldehyde derived from D-phenylalanine. The toluene was removed under reduced pressure and the residue was chased with additional toluene (3×50 mL). The resulting oil was then dissolved in 40 mL of THF and 35.6 mL (17.8 mmol) of a 0.5M solution of KHMDS in toluene added. The resulting solution was allowed to stir for 10 min then quenched by the addition of 100 mL of EtOAc and 100 mL of a 10% aqueous NaHSO$_4$ solution. The organic extract was then washed with a 10% aqueous NaHSO$_4$ solution (2×100 mL) followed by a saturated aqueous NaHCO$_3$ solution (2×100 mL). The organic phase was dried over anhydrous MgSO$_4$ and concentrated under reduced pressure to afford an oil. Flash chromatography of the residue on silica gel using hexanes/ EtOAc (7:3) as solvent system provided 1.50 g (72% yield) of product which could be crystallized from slow evaporation from ether: mp 127°–129° C.; $[\alpha]_D^{21}$ –50.2° (c 1.26, CHCl$_3$; IR (CHCl$_3$) 3480 (m), 3470 (w), 3415 (w); 2990 (m), 1745 (s), 1705 (s), 1660 (m), 1580 (m), 1490 (s), 1380 (m), 1165 (s) cm$^{-1}$; $^1$H NMR (500 MHz, CDCl$_3$) d 8.25 (d, J=3.5 Hz, 1 H), 7.24–7.18 (m, 3 H), 7.07–7.05 (m, 2 H), 6.38 (br s, 1 H), 5.17 (br s, 1 H), 4.94 (t, J=5.8 Hz, 1 H), 3.78 (d, J =13.4 Hz, 1 H), 3.71 (s, 3H), 3.39 (d, J=13.3 Hz, 1 H), 2.41 (dd, J=14.3 and 7.1 Hz, 1 H), 2.28 (dd, J=15.0 and 8.2 Hz, 1 H), 1.99–1.93 (m, 1 H) 1.65 (s, 3 H), 1.57 (s, 3H), 1.43 (s, 9 H), 0.93 (d, J=6.8 Hz, 3 H), 0.82 (d, J=6.7 Hz, H); $^{13}$C NMR (125 MHz, CDCl$_3$) d 202.00, 172.64, 162.98, 54.37, 135.99, 134.60, 130.04 (2C), 127.82 (2C), 126.62, 17.00, 110.40, 78.87, 73.18, 60.54, 52.17, 39.39, 33.38, 2.99, 28.29 (3C), 25.71, 17.86, 16.89, 15.96; high resolution mass spectrum (CI, methane) m/z 471.2838 [(M+H)$^+$; calculated for C$_{27}$H$_{39}$N$_2$O$_5$: 471.2859]. Analysis calculated for C$_{27}$H$_{38}$N$_2$O$_5$: C, 68.91; H, 8.14; N, 5.95; found: C, 68.85; H, 8.15; N, 5.92.

D. Val (ald)-Phe-Boc, [5 (S)-ethanal-(5-isopropyl) pyrolin-4one-3]-2(S)-Boc-amino-(2-benzyl) acetate methyl ester A solution of 1.25 g (2.66 mmol) of Val-Phe-Boc in 90 mL of an acetone:H$_2$O (8:1) solution was treated with 622 mg (5.31 mmol) of NMO and a few crystals (ca.5 mg) of OsO$_4$. The mixture was allowed to stir for 24 h after which time the reaction was quenched with 25 mL of a 10% aqueous NaHSO$_3$ solution and 50 mL of EtOAc. The organic layer was washed further with a 10% aqueous NaHSO$_3$ solution (2×25 mL) followed by a saturated aqueous NaCl solution (2×25 mL). The organic layer was then dried over MgSO$_4$, filtered, and concentrated under reduced pressure to afford an oil. Flash chromatography (silica, 50→100% gradient elution: EtOAc/hexanes) provided 1.32 g (96% yield) of product which was dissolved in 15 mL of benzene and treated with 1.0 g of K$_2$CO$_3$ and 1.47 g (3.32 mmol) of lead tetraacetate. The reaction mixture was allowed to stir for 10 min and then quenched with 50 mL of H$_2$O and 50 mL of EtOAc. The organic layer was then washed with a saturated aqueous NaHCO$_3$ solution (3×50 mL), dried over MgSO$_4$, filtered, and concentrated under reduced pressure to afford an oil which could be crystallized by the addition of Et$_2$O and storing at 5° C. to afford 904 mg of colorless crystalline solid. Flash chromatography (silica, 50% EtOAc/hexanes) of the filtrate provided an additional 73 mg (83% overall yield from olefin) of product which was crystallized from ethyl ether at 0° C.: mp 156°–158° C.; $[\alpha]_D^{24}$ –35.0° (c 1.00, CHCl$_3$); IR (CHCl$_3$) 3450 (w), 3480 (W), 2980 (W); 1750 (m), 1725 (s), 1705 (s), 1675 (m) 1580 (w), 1490 (s), 1160 (s) cm$^{-1}$; $^1$H NMR (500 MHz, CDCl$_3$) d 9.33 (d, J=3.6 Hz, 1 H), 8.32 (br s, 1 H), 7.24–7.21 (m, 3 H), 7.03–7.02 (m, 2 H), 6.25 (br s, 1 H), 5.91 (br s, 1 H), 3.83 (d, J=13.2 Hz, 1 H), 3.73 (s, 3 H), 3.35 (d, J=13.1 Hz, 1 H), 2.74 (dd, J=15.6 and 3.9 Hz, 1 H), 2.63 (d, J= 15.5 Hz, 1 H), 2.09–2.03 (m, 1 H), 1.43 (s, 9 H), 0.95 (d, J =6.9 Hz, 3 H), 0.84 (d, J=6.7 Hz, 3 H); $^{13}$C NMR (62.5 MHz, CDCl$_1$) d 199.94, 199.85, 172.17, 163.92, 154.09, 135.52, 129.89 (2C), 128.02 (2C), 126.90, 111.71, 79.14, 70.89, 60.03, 52.52, 48.19, 39.19, 33.96, 28.23 (3C), 16.79, 15.56; high resolution mass spectrum (CI, methane) m/z 445.2312 [(M+H)$^+$; calculated for C$_{24}$H$_{33}$N$_2$O$_6$: 445.2338]. Analysis calculated for C$_{24}$H$_{32}$N$_2$O$_6$: C, 64.85; H, 7.26; N, 6.30; found: C, 64.85; H, 7.40; N, 6.39.

E. Leu-Val-Phe-Boc, [5 (S)-prenyl-(5-isobutyl) pyrrolin-4-one-3]-[5 (S) -(5-isopropyl) pyrroline-4-one-3]-2 (S)-Boc-amino-2-benzyl acetate methyl ester A solution of 600 mg (2.81 mmol) of the amine derived from D-leucine in 25 mL of dry toluene was treated with a 25 mL toluene solution of 1.25 g (2.81 mmol) of the Val-Phe-Boc aldehyde. The toluene was removed under reduced pressure and the residue was chased with additional toluene (4×50 mL). The resulting oil was then dissolved in 100 mL of THF and 56.2 mL (28.1 mmol) of a 0.5M solution of KHMDS in toluene added. The resulting solution was allowed to stir for 10 min then quenched by the addition of 100 mL of EtOAc and 100 mL of a 10% aqueous $NaHSO_4$ solution. The organic extract was then washed with a 10% aqueous $NaHSO_4$ solution (2×100 mL) followed by a saturated aqueous $NaHCO_3$ solution (2×100 mL). The organic phase was dried over anhydrous $MgSO_4$ and concentrated under reduced pressure to afford an oil. Flash chromatography (silica, 30→75% gradient elution: EtOAc/hexanes) provided 744 mg (44% yield) of product which could be crystallized from slow evaporation from ether as well as 445 mg (36% recovery) of starting material: mp 164°–165° C.; $[\alpha]_D^{21}$ −180° (c 0.50, $CHCl_3$); IR ($CHCl_3$) 3450 (w), 3420 (w), 3350 (w), 2975 (m), 1740 (m), 1705 (s), 1645 (s) 1575 (s), 1485 (S), 1450 (m), 1165 (s) $cm^{-1}$; $^1H$ NMR (500 MHz, $CDCl_3$) d 8.23 (d, J=3.5 Hz, 1 H), 8.19 (d, J=4.0 Hz, 1 H), 7.53 (d, J=3.4 Hz, 1 H), 7.18–7.17 (m, 3 H), 7.01–7.00 (m, 2 H), 6.51 (br s, 1 H), 5.43 (br s, 1 H), 4.97 (t, J=7.3 Hz, 1 H), 3.73 (s, 3 H), 3.71–3.69 (m, 1 H), 3.42 (d, J=13.2 Hz, 1 H), 2.34 (dd, J=14.4 and 7.9 Hz, H), 2.26 (dd, J=14.3 and 6.8 Hz, H), 2.02–1.96 (m, 1 H), 1.69–1.59 (m, 4 H), 1.59 (s, 3 H), 1.54–1.50 (m, 2 H), 1.41 (s, 9 H), 0.92 (d, J=6.8 Hz, 3 H), 0.84 (d, J=5.9 Hz, 3 H), 0.80 (d, J=6.7 Hz, 3 H), 0.76 (d, J=5.7 Hz, 3 H); $^{13}C$ NMR (62.5 MHz, $CDCl_3$) d 203.79, 201.03, 72.77, 163.80, 160.69, 154.22, 136.19, 135.93, 130.16 (2C), 27.87 (2C), 126.66, 117.23, 110.48, 108.21, 78.89, 71.38, 1.25, 60.45, 52.43, 44.91, 39.89, 37.82, 35.62, 28.39 (3C), 5.88, 24.63, 24.16, 23.63, 18.12, 16.97, 15.98; high resolution mass spectrum (CI, methane) m/z 608.3701 $[(M+H)^+$; calculated for $C_{35}H_{50}N_3O_6$: 608.3699].

F. Leu(ald)-Val-Phe-Boc, [5(S) ethanal–5(-isobutal) pyrrolin-4-one-3]-[5(S) -(5-isopropal) pyrrolin-4-one-3]-2(S)-Boc-amino-2-benzyl acetate methyl ester A solution of 750 mg (1.23 mmol) of Leu-Val-Phe-Boc in 45 mL of an acetone:$H_2O$ (8:1) solution was treated with 289 mg (2.47 mmol) of N-methylmorpholine N-oxide monohydrate (NMO) and a few crystals (ca. 5 mg) of $OsO_4$. The mixture was allowed to stir for 24 h after which time the reaction was quenched with 25 mL of a 10% aqueous $NaHSO_3$ solution and 50 mL of EtOAc. The organic layer was washed further with a 10% aqueous $NaHSO_3$ solution (2×25 mL) followed by a saturated aqueous NaCl solution (2×25 mL). The organic layer was then dried over $MgSO_4$, filtered, and concentrated under reduced pressure to afford an oil. Flash chromatography (silica, 50→100% gradient elution: EtOAc/hexanes) provided product which was dissolved in 10 mL of benzene and treated with 750 mg of $K_2CO_3$ and 684 mg (1.54 mmol) of lead tetraacetate. The reaction mixture was allowed to stir for 10 min and then quenched with 50 mL of $H_2O$ and 50 mL of EtOAc. The organic layer was then washed with a saturated aqueous $NaHCO_3$ solution (3×50 mL), dried over $MgSO_4$, filtered, and concentrated under reduced pressure to afford an oil which could be crystallized by the addition of $Et_2O$ and storing at 5° C. to afford 457 mg (64% yield) of colorless crystalline solid. Flash chromatography (silica, 50% EtOAc/hexanes) of the filtrate provided an additional 95 mg (13%, 77% total yield) of product which was crystallized from ethyl ether at 0° C.: mp 197°–200° C.; $[\alpha]_D^{21}$ −169° (c 1.00, $CHCl_3$); IR ($CHCl_3$) 3450 (w), 2975 (m), 1730 (m), 1705 (s), 1650 (s) 1575 (s), 1490 (s), 1450 (m), 1165 (s) $cm^{-1}$; $^1H$ NMR (500 MHz, $CDCl_3$) d 9.68 (d, J =1.6 Hz, 1 H), 8.27–8.26 (m, 2 H), 7.38 (br s, 1 H), 7.20–7.19 (m, 3 H), 7.02–7.00 (m, 2 H), 6.36 (br s, 1 H), 6.21 (br s, 1 H), 3.77–3.73 (m, 4 H), 3.38 (d, J=13.1 Hz, 1 H), 2.87 (dd, J=17.5 and 1.8 Hz, 1 H), 2.55 (d, J=17.5 Hz, 1 H), 2.04–1.98 (m, 1 H), 1.76 (dd, J=14.0 and 4.7 Hz, 1 H), 1.56 (d, J=14.0 and 7.7 Hz, 1 H), 1.41 (s, 9 H), 0.93 (d, J=6.8 Hz, 3 H), 0.83 (d, J=6.6 Hz, 3 H), 0.80 (d, J=6.7 Hz, 3 H), 0.72 (d, J=6.5 Hz, 3 H); $^{13}C$ NMR (62.5 MHz, $CDCl_3$) d 202.33, 200.80, 199.67, 172.65, 164.13, 161.04, 154.14, 136.02, 130.08 (2C), 127.96 (2C), 126.78, 110.97, 107.70, 78.94, 70.97, 68.00, 60.21, 52.52, 49.57, 44.10, 39.77, 38.15, 28.39 (3C), 24.42, 24.12, 23.56, 17.39, 15.93; high resolution mass spectrum (CI, methane) m/z 582.2195 $[(M+H)^+$; calculated for $C_{32}H_{44}N_3O_7$: 582.3179]. Analysis calculated for $C_{32}H_{43}N_3O_7$: C, 66.07; H, 7.45; N, 7.22; found: C, 65.92; H, 7.47; N, 6.99.

G. Leu-Leu-Val-Phe-Boc, [5 (S)-prenyl-(5-isobutyl) pyrrolin-4-one-3]-[5(S)-(5-isobutyl)pyrrolin-4-one-3]-[5 (S)-(5-isopropyl) pyrrolin-4-one-3]-2 (S)-Boc-amino-2-benzyl acetate methyl ester A solution of 175 mg (0.819 mmol) of the amine derived from D-leucine in 25 mL of dry toluene was treated with a 25 mL chloroform solution of 500 mg (0.860 mmol) of the Leu-Val-Phe-Boc aldehyde. The solvent was removed under reduced pressure and the residue was chased with additional toluene (4×50 mL). The resulting oil was then dissolved in 30 mL of THF and 16.4 mL (8.19 mmol) of a 0.5M solution of KHMDS in toluene added. The resulting solution was allowed to stir for 15 min then quenched by the addition of 100 mL of EtOAc and 100 mL of a 10% aqueous $NaHSO_4$ solution. The organic extract was then washed with a 10% aqueous $NaHSO_4$ solution (2×100 mL) followed by a saturated aqueous $NaHCO_3$ solution (2×100 mL). The organic phase was dried over anhydrous $MgSO_4$ and concentrated under reduced pressure to afford an oil. Flash chromatography (silica, gradient elution 30→75%: EtOAc/hexanes) provided 397 mg (59% yield) of product, which could be crystallized from slow evaporation from ether, as well as 159 mg (29% recovery) of starting material: mp 194°–196° C.; $[\alpha]_D^{24}$ −284° (c 1.00, $CHCl_3$); IR ($CHCl_3$) 3450 (w), 3420 (w), 3350 (w), 2960 (m), 1740 (m), 1705 (s), 1645 (s), 1575 (s), 1490 (m), 1450 (m), 1365 (m), 1165 (s) $cm^{-1}$; $^1H$ NMR (500 MHz, $CDCl_3$) d 8.23 (d, J=3.1 Hz,1 H), 8.20 (d, J=4.2 Hz, 1 H), 8.15 (d, J=3.8 Hz, 1 H), 7.51–7.49 (m, 2 H), 7.19–7.17 (m, 3 H), 7.01–6.99 (m, 2 H), 6.57 (br s, 1 H), 5.34 (d, J= 4.1 Hz, 1 H), 4.97 (t, J=7.3 Hz, 1 H), 3.73 (s, 3 H), 3.66 (d, J=13.0 Hz, 1 H), 3.44 (d, J=13.1 Hz, 1 H), 2.34 (dd, J=14.6 and 8.0 Hz, 1 H), 2.24 (dd, J=14.2 and 7.1 Hz, 1 H), 1.97–1.92 (m, 1 H), 1.80 (dd, J=14.1 and 4.0 Hz, 1 H), 1.68 (s, 3 H), 1.64–1.60 (m, 8 H), 1.41 (s, 9 H), 0.85 (d, J =6.8 Hz, 6 H), 0.82 (d, J=6.5 Hz, 3 H), 0.79 (d, J=6.7 Hz, 3 H), 0.74 (d, J=6.7 Hz, 3 H), 0.67 (d, J=6.6 Hz, 3 H); $^{13}C$ NMR (62.5 MHz, $CDCl_3$) d 203.36, 202.67, 201.09, 172.66, 163.91, 161.70, 159.96, 154.27, 136.19, 136.08, 130.17 (2C), 127.90 (2C), 126.70, 116.87, 110.68, 109.79, 107.02, 78.97, 71.40, 71.24, 68.80, 60.56, 52.46, 47.57, 44.89, 40.07, 37.84, 36.23, 28.37 (3C), 25.92, 24.69 (2C), 24.33, 24.28, 23.54 (2C), 18.10, 17.08, 15.89; high resolution mass spectrum (CI, methane) m/z 744.4433 [M$^+$; calculated for $C_{43}H_{60}N_4O_7$: 744.4462]. Analysis calculated for $C_{43}H_{60}N_4O_7$: C, 69.33; H, 8.11; N, 7.52; found: C, 69.28; H, 8.19; N, 7.43.

H. Leu (ald)-Leu-Val-Phe-Boc, [5 (S)-ethanal-(5-isobutyl) Pyrrolin-4-one-3]-[5 (S)-(5-isobutyl) pyrrolin-4-one-3]-[5 (S)-(5-isopropyl) pyrroline-4-one-3]-2 (S)-Boc-amino-2-benzyl acetate methyl ester A solution of 340 mg (0.456 mmol) of Leu-Leu-Val-Phe-Boc in 20 mL of an acetone:$H_2O$ (8:1) solution was treated with 107 mg (0.913 mmol) of NMO and a few crystals (ca. 5 mg) of $OsO_4$. The mixture was allowed to stir for 48 h after which time the reaction was quenched with 20 mL of a 10% aqueous $NaHSO_3$ solution and 20 mL of EtOAc. The organic layer was washed further with a 10% aqueous $NaHSO_3$ solution (2×10 mL) followed by a saturated aqueous NaCl solution (2×10 mL). The organic layer was then dried over $MgSO_4$, filtered, and concentrated under reduced pressure to afford an oil. Flash chromatography (silica, 50→100% gradient elution: EtOAc/hexanes) provided product which was dissolved in 10 mL of benzene and treated with 350 mg of $K_2CO_3$ and 253 mg (0.571 mmol) of lead tetraacetate. The reaction mixture was allowed to stir for 10 min and then quenched with 20 mL of $H_2O$ and 20 mL of EtOAc. The organic layer was then washed with a saturated aqueous $NaHCO_3$ solution (3×20 mL), dried over $MgSO_4$, filtered, and concentrated under reduced pressure to afford an oil which could be crystallized by the addition of $Et_2O$ and storing at 0° C. to afford 122 mg (37% yield) of colorless crystalline solid. Flash chromatography (silica, EtOAc) of the filtrate provided an additional 42 mg (13%, 50% total yield) of product which was crystallized from ethyl ether at 0° C.: mp 203°–205° C.; $[\alpha]_D^{26}$ –219° (c 1.65, $CHCl_3$); IR ($CHCl_3$) 3450 (w), 3420 (w), 3350 (w), 2970 (In), 1730 (s), 1710 (s), 1650 (s) 1580 (s), 1490 (m), 1450 (m), 1165 (s) cm$^{-1}$; $^1$H NMR (500 MHz, $CDCl_3$) d 9.69 (d, J=1.6 Hz, 1 H), 8.24 (app d, J=4.1 Hz, 2 H), 8.17 (d, J=3.9 Hz, 1 H), 7.50 (br d, J= 2.7 Hz, 1 H), 7.33 (br s, 1 H), 7.19–7.18 (in, 3 H), 7.01–6.98 (m, 2 H), 6.54 (br s, 1 H), 6.27 (d, J=4.0 Hz, 1 H), 3.73 (s, 3 H), 3.67 (d, J=13.1 Hz, 1 H), 3.43 (d, J=13.1 Hz, 1 H), 2.89 (dd, J=17.8, 1.7 Hz, 1 H), 2.54 (d, J=17.7 Hz, 1 H), 1.98–1.93 (m, 1 H), 1.82 (dd, J=13.6, 3.9 Hz, 1 H), 1.78 (dd, J=14.1, 5.0 Hz, 1 H), 1.62 (d, J=14.1, 7.4 Hz, 1 H), 1.57–1.49 (m, 2 H), 1.39–1.35 (m, 10 H), 0.87–0.84 6 H), 0.82–0.79 (m, 6 H), 0.75 (d, J=6.7 Hz, 1 H), 0.66 (d, J=6.6 Hz, 3 H ); $^{13}$C NMR (62.5 MHZ, $CDCl_3$) d 202.32, 201.83, 200.90, 199.63, 172.66, 163.92, 161.73, 160.49, 154.21, 136.02, 130.12 (2C), 127.89 (2C), 126.69, 110.55, 108.96, 107.06, 78.96, 71.09, 68.33, 68.09, 60.48, 52.44, 49.80, 7.41, 44.03, 39.99, 37.76, 28.34 (3C), 24.67, 24.54, 24.12 (2C), 23.59, 23.49, 17.04, 15.84; high resolution mass spectrum (CI, $NH_3$) m/z 718.3906 [M$^+$; calculated for $C_{40}H_{54}N_4O_8$ 18.3941].

I. Phe-Leu-Leu-Val-Phe-Boc, [5 (S)-prenyl-(5-benzyl) pyrrolin-4-one-3]-[5(S)-(5-isobutyl)pyrrolin-4-one-3]- [5(S)-(5-isobutyl) pyrrolin-4-one-3]-[5(S)-(5-isopropyl) pyrrolin-4-one-3]-2(S)-Boc-amino-2-benzyl acetate methyl ester A solution of the amine derived from D-leucine in dry toluene is treated with a chloroform solution of the Leu-Val-Phe-Boc aldehyde. The toluene is removed under reduced pressure and the residue chased with additional toluene. The resulting oil is then dissolved in of THF and a 0.5M solution of KHMDS in toluene is added. The resulting solution is allowed to stir for 15 min then quenched by the addition of EtOAc and a 10% aqueous $NaHSO_4$ solution. The organic extract is then washed with a 10% aqueous $NaHSO_4$ solution followed by a saturated aqueous $NaHCO_3$ solution. The organic phase is dried over anhydrous $MgSO_4$ and concentrated under reduced pressure to afford structure (25) as an oil. Flash chromatography (silica, gradient elution, EtOAc/hexanes) provides product which can be crystallized by slow evaporation from ether as well starting material.

EXAMPLE 14

Phe-Leu-Leu-Boc, [5(S)-prenyl-(5-benzyl) pyrrolin-4-one-3]-[5(S)-(5-isobutyl) pyrrolin-4 -one-3]-2(acetate methyl ester A solution of 225 mg (0.586 mmol) of the Phe-leu amine in 10 mL of dry toluene was treated with a 10 mL toluene solution of 185 mg (0.645 mmol) of the D-leucine derived aldehyde. The toluene was removed under reduced pressure and the residue was chased with additional toluene (4×10 mL). The resulting oil was then dissolved in 35 mL of a 1:1.5 N,N,N',N'-tetramethylenediamine (TMEDA)/THF mixture and 9.4 mL (4.69 mmol) of a 0.5M solution of KHMDS in toluene added. The resulting solution was allowed to stir for 15 min then quenched by the addition of 50 mL of EtOAc and 50 mL of a 10% aqueous $NaHSO_4$ solution. The organic extract was then washed with a 10% aqueous $NaHSO_4$ solution (4×50 mL) followed by a saturated aqueous $NaHCO_3$ solution (2×50 mL). The organic phase was dried over anhydrous $MgSO_4$ and concentrated under reduced pressure to afford an oil. Flash chromatography (silica, 20%: EtOAc/hexanes) provided 111 mg (30% yield) of product: 1H NMR (500 MHz, $CDCl_3$) d 8.06 (br s, 1 H), 7.99 (br s, 1 H), 7.24–7.17 (m, 3 H), 7.14 (br s, 1 H), 7.05 (d, J= 6.1 Hz, 2 H), 6.80 (br s, 1 H), 5.33 (br s, I H), 4.89 (d, J =7.6 Hz, 1 H), 3.68 (s, 3 H), 2.81 (d, J=13.6 Hz, 1 H), 2.72 (d, J=13.6 Hz, 1 H), 2.46 (dd, J=21.4 and 7.8 Hz, 1 H), 2.24–2.18 (m, 2 H), 1.84 (dd, J=13.1 and 3.8 Hz, 1 H), 1.63 (s, 3 H), 1.58–1.50 (m, 7 H), 1.39 (s, 9 H), 0.84 (d, J=6.5 Hz, 3 H), 0.82 (d, J=6.7 Hz, 6 H), 0.80 (d, J=6.3 Hz, 3 H); high resolution mass spectrum (CI, $NH_3$) m/z 622.3821 [(M+H)$^+$; calculated for $C_{36}H_{52}N_3O_6$: 622.3856].

EXAMPLE 15

A. Val-Phe-NH$_2$, [5 (S)-prenyl-(5-isopropyl) pyrrolin-4-one-3]-2(S)-amino-2-benzyl acetate methyl ester A solution of 200 mg (0.425 mmol) of the Val-Phe-Boc pyrrolinone in 5.0 mL of $CH_2Cl_2$ was treated with 91.1 mg (0.850 mmol) of 2,6-lutidine and 189 mg (0.850 mmol) of TMSOTf. The reaction mixture was stirred for 15 min and then quenched by the addition of 50 mL of $CH_2Cl_2$ followed by 50 mL of a saturated aqueous $NaHCO_3$ solution. The organic layer was then washed further with an aqueous $NaHCO_3$ solution (2×50 mL), dried over anhydrous $MgSO_4$ and concentrated to afford a crude oil. Flash chromatography (silica, 50→100% gradient elution: EtOAc/hexanes) provided 32.2 mg (77% yield) of amine: high resolution mass spectrum (CI, methane) m/z 371.2322 [(M+H)$^+$; calculated for $C_{22}H_{31}N_2O_3$: 371.2334].

35

B. Val-Phe-Cap, [5 (S)-prenyl-(5-isopropyl) pyrrolin-4-one-3]-[5 (S)-(5-benzyl) pyrrolin-4-one-3]-benzyl A solution of 530 mg (1.43 mmol) of the Val-Phe-amine in 25 mL of dry toluene was treated with a 25 mL toluene solution of 202 mg (1.50 mmol) of hydrocinnamaldehyde. The toluene was removed under reduced pressure and the residue was chased with additional toluene (2×50 mL). The resulting oil was then dissolved in 50 mL of THF and 14.3 mL (7.16 mmol) of a 0.5M solution of KHMDS in toluene added. The resulting solution was allowed to stir for 15 min then quenched by the addition of 100 mL of EtOAc and 100 mL of a 10% aqueous $NaHSO_4$ solution. The organic extract was then washed with a 10% aqueous $NaHSO_4$ solution (2×100 mL) followed by a saturated aqueous $NaHCO_3$ solution (2×100 mL). The organic phase was dried over anhydrous $MgSO_4$ and concentrated under reduced pressure to afford an oil. Flash chromatography (silica, gradient elution 30→50%: EtOAc/hexanes) provided 443 mg (68% yield) of product which could be crystallized from slow evaporation from ether: mp 150°–151° C.; $[\alpha]_D^{21}$–156° (C 0.500, $CHCl_3$); IR ($CHCl_3$) 3450 (m), 3010 (w), 2980 (w); 1650 (s), 1585 (s), 1455 (m), 1160 (m) $cm^{-1}$; $^1H$ NMR (500 MHz, $CDCl_3$) d 8.36 (d, J=3.9 Hz, 1 H), 7.36 (d, J=3.0 Hz, 1 H), 7.25–7.05 (m, 9 H), 6.81–6.80 (m, 2 H), 5.35 (br s, 1 H), 4.99 (br t, 1 H), 3.39 (d, J=16.0 Hz, 1 H), 3.27 (d, J=15.9 Hz, 1 H), 3.13 (d, J=13.2 Hz, 1 H), 3.03 (d, J=13.2 Hz, 1 H), 2.45–2.35 (m, 2 H), 1.99–1.94 (m, 1 H), 1.65 (d, J=19.3 Hz, 6 H), 0.92 (d, J=6.8 Hz, 3 H), 0.73 (d, J=6.6 Hz, 3 H); $^{13}C$ NMR (125 MHz, $CDCl_3$) d 204.01, 201.65, 162.70, 161.23, 140.40, 135.34, 135.07, 130.19 (2C), 128.12 (3C), 128.06 (2C), 127.55, 126.42, 125.56, 116.93, 111.96, 110.09, 73.68, 67.82, 44.25, 33.45, 33.05, 27.90, 25.84, 18.05, 16.89, 16.19; high resolution mass spectrum (CI, methane) m/z 455.2729 [(M+H)$^+$; calculated for $C_{30}H_{35}N_2O_2$: 4455.2698]. Analysis calculated for $C_{30}H_{34}N_2O_2$: C, 79.26; H, 7.54; N, 6.16; found: C, 78.97; H, 7.25; N, 5.89.

C. Leu-Val-Phe-$NH_2$, [5 (S)-prenyl-(5-isobutyl)pyrrolin-4-one-3] -[5 (S)-(5-isoprypyl)pyrrolin-4-one-3] -2(6)-amino-2-benzyl acetate methyl ester A solution of 50.0 mg (0.743 mmol) of the Leu-Val-Phe-Boc pyrrolinone in 3.0 mL of $CH_2Cl_2$ was treated with 22.0 mg (0.206 mmol) of 2,6-lutidine and 36.6 mg (0.165 mmol) of TMSOTf. The reaction mixture was stirred for 15 min and then quenched by the addition of 10 mL of $Et_2O$ followed by 10 mL of a saturated aqueous $NaHCO_3$ solution. The organic layer was then washed further with an aqueous $NaHCO_3$ solution (2×10 mL), dried over anhydrous $MgSO_4$ and concentrated to afford a crude oil. Flash chromatography (silica, 100% EtOAc) provided 32.2 mg (77% yield) of amine: IR ($CHCl_3$) 3450 (w), 3360 (w), 2960 (m), 1740 (m), 1650 (s), 1575 (s), 1440 (w), 1175 (m), 905 (w) $cm^{-1}$; $^1H$ NMR (500 MHz, $CDCl_3$) d; $^{13}C$ NMR (62.5 MHz, $CDCl_3$) d 203.66, 202.24, 175.32, 162.27, 161.27, 135.60, 135.50, 130.01 (2C), 128.28 (2C), 127.02, 117.31, 114.32, 107.55, 71.71, 71.29, 59.38, 52.04, 44.97, 44.39, 37.81, 35.58, 25.80, 24.54, 24.18, 23.51, 18.09, 17.00, 16.01; high resolution mass spectrum (CI, methane) m/z 506.3012 [(M—

36

H)$^+$; calculated for $C_{30}H_{40}N_3O_4$: 506.3020].

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having structure:

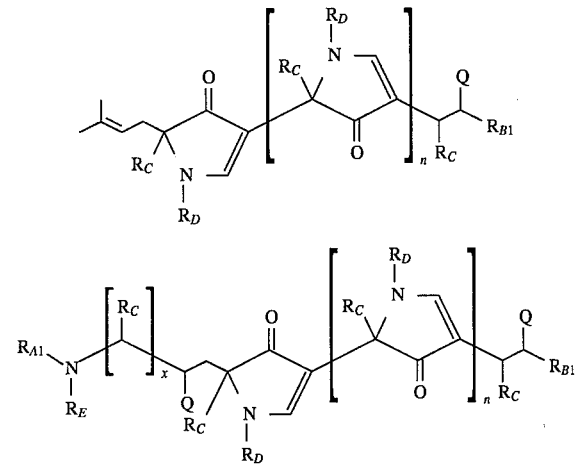

wherein:

$R_{A1}$ is H, a C-terminal amino acid, a C-terminal peptide, an amine protecting group, an amide protecting group, a group that improves the pharmacokinetic properties of the compound, or a group that improves the pharmacodynamic properties of the compound;

$R_{B1}$ is $OR_D$, $NR_DR_D$, a N-terminal amino acid, a N-terminal peptide, a carboxyl protecting group, a group that improves the pharmacokinetic properties of the compound, or a group that improves the pharmacodynamic properties of the compound;

each $R_C$ is, independently, an amino acid side chain;

$R_D$ is H, an amine protecting group, or alkyl having 1 to about 7 carbon atoms;

$R_E$ is H or an amine protecting group, or $R_{A1}$ and $R_E$, together are a group that improves the pharmacokinetic properties of the compound or a group that improves the pharmacodynamic properties of the compound;

each Q is, independently, OH or =O;

x is 0 or 1; and n is 1–200.

2. The compound of claim 1 wherein $R_{A1}$—N—$R_E$ together are morpholino.

3. The compound of claim 1 wherein $R_{B1}$ is NH—CH($CH_2$—$C_6H_{11}$)—CH(OH)—CH(OH)—$CH_2$—CH($CH_3$)$_2$.

4. The compound of claim 1 wherein $R_{A1}$ s C(O)O—t—butoxyl.

5. The compound of claim 1 wherein $R_{B1}$ is $NH_2$.

6. A compound having structure:

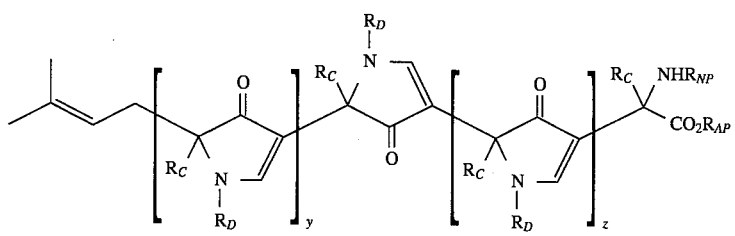

wherein:

each $R_C$ is, independently, an amino acid side chain;

$R_D$ is H, an amine protecting group, or alkyl having 1 to about 7 carbon atoms;

$R_{NP}$ is H or an amine protecting group;

$R_{AP}$ is H or a carboxyl protecting group; and y and z are, independently, 1–200.

7. A compound having structure:

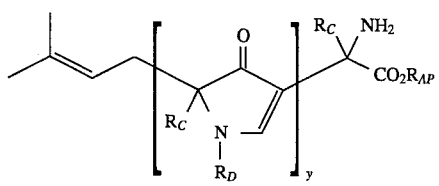

wherein:

each $R_C$ is, independently, an amino acid side chain;

$R_D$ is H, an amine protecting group, or alkyl having 1 to about 7 carbon atoms;

$R_{NP}$ is H or an amine protecting group;

$R_{AP}$ is H or a carboxyl protecting group; and y is 2–200.

8. A compound having structure:

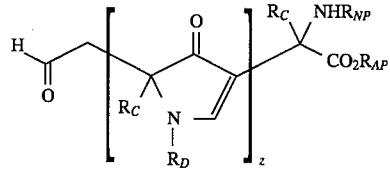

wherein:

each $R_C$ is, independently, an amino acid side chain;

$R_D$ is H, an amine protecting group, or alkyl having 1 to about 7 carbon atoms;

$R_{NP}$ is H or an amine protecting group;

$R_{AP}$ is H or a carboxyl protecting group; and z is 2–200.

9. A process for preparing a compound having structure:

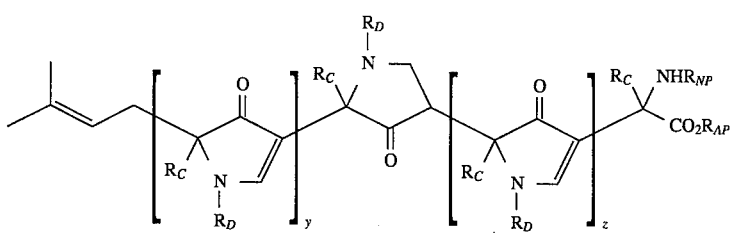

comprising the steps of:

providing a first synthon having structure:

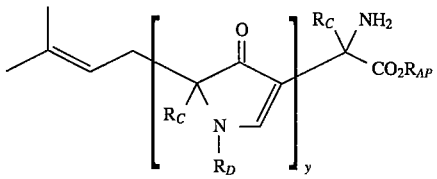

contacting said first synthon with a second synthon having structure:

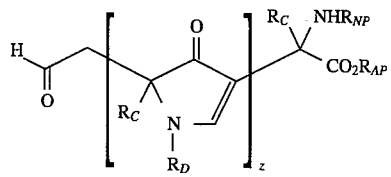

for a time and under reaction conditions effective to form said compound;

wherein:

each $R_C$ is, independently, an amino acid side chain;

$R_D$ is H, an amine protecting group, or alkyl having 1 to about 7 carbon atoms;

$R_{NP}$ is H or an amine protecting group;

$R_{AP}$ is H or a carboxyl protecting group; and y and z are, independently, 0–200.

10. A composition comprising the compound of claim 1 in a pharmaceutically acceptable carrier.

11. A composition comprising the compound of claim 6 in a pharmaceutically acceptable carrier.

12. A method for mimicking or inhibiting the chemical activity of a peptide, comprising providing in place of the peptide at least one chemical compound according to claim 1.

13. A method for inhibiting the chemical activity of an enzyme, comprising contacting said enzyme with at least one chemical compound according to claim 1.

* * * * *

UNITED STATES PATENT AND TRADEMARK OFFICE
CERTIFICATE OF CORRECTION

PATENT NO. : 5,489,692

DATED : FEBRUARY 6, 1996

INVENTOR(S) : Hirschmann et al

Page 1 of 2

It is certified that error appears in the above-indentified patent and that said Letters Patent is hereby corrected as shown below:

Col. 2, line 60, after "about" insert a space before --7--.
Col. 4, line 56, after "having" insert --1--.
Col. 9, line 64, after "been" delete the "s" and insert --shown by Iizuka,--.
Col. 16, line 10, after "1" insert a space.
Col. 18, line 28, change the equation "$C^{11}H_{21}NO_2$" to $C_{11}H_{21}NO_2$--.
Col. 18, line 57, change "$^{13}C$" to --(3C)--.
Col. 20, line 62, change "135,082" to --135.082--.
Col. 22, line 19, change "5.63" to --45.63--.
Col. 23, line 63, change "-C" to --$^{13}C$--.
Col. 24, line 19, change "$^1H$" to --1 H--.
Col. 25, line 36, change "rain" to --min --.
Col. 26, line 29, change "340" to --840--.
Col. 26, line 40, change "(8)" at the end of line 1 to --(S)--.
Col. 26, line 62, after "1660" delete "835"; same line, change "1530" to --1580--; same line, at the end of the line change "1330" to --1380--.

UNITED STATES PATENT AND TRADEMARK OFFICE
CERTIFICATE OF CORRECTION

PATENT NO. : 5,489,692
DATED : February 6, 1996
INVENTOR(S) : Hirschmann et al.

It is certified that error appears in the above-indentified patent and that said Letters Patent is hereby corrected as shown below:

Col. 27, line 2, at the end of the line change "S)" to --H)--.
Col. 28, line 10, change "384.3 114" to --384.3114--.
Col. 30, line 15, at the end of the line change "17.00" to --117.00--.
Col. 30, line 16, change "2.99" near the end of the line to --32.99--.
Col. 31, line 36, change "72.77" to --172.77--.
Col. 31, line 37, change "27.87" to --127.87--.
Col. 31, line 38, change "1.25" to --71.25--.
Col. 31, line 39, change "5.88" to --25.88--.
Col. 33, line 48, change "0.84 6H" to --0.84 (m, 6 H)--.
Col. 33, line 54, change "7.41" to --47.41--.
Col. 33, line 57, change "18.3941" to --718.3941--.
Col. 34, line 38, change "1H" to --$^{1}$H--.

Signed and Sealed this

Twenty-ninth Day of April, 1997

BRUCE LEHMAN

Attest:

Attesting Officer

Commissioner of Patents and Trademarks